US012035942B2

(12) United States Patent
Jones et al.

(10) Patent No.: US 12,035,942 B2
(45) Date of Patent: *Jul. 16, 2024

(54) SURGICAL CANNULA WITH REMOVABLE PRESSURE SEAL

(71) Applicant: Embody, Inc., Norfolk, VA (US)

(72) Inventors: Christopher K. Jones, Colorado Springs, CO (US); Douglas Snell, South Portland, ME (US); Isaac Running, Bozeman, MT (US); R. Sean Churchill, Mequon, WI (US); Nathan Kemper, Virginia Beach, VA (US)

(73) Assignee: Embody, Inc., Norfolk, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/158,188

(22) Filed: Jan. 23, 2023

(65) Prior Publication Data

US 2023/0157724 A1 May 25, 2023

Related U.S. Application Data

(63) Continuation of application No. 17/173,531, filed on Feb. 11, 2021, now Pat. No. 11,559,330.

(Continued)

(51) Int. Cl.
*A61B 17/34* (2006.01)
*A61F 2/46* (2006.01)

(52) U.S. Cl.
CPC ...... *A61B 17/3462* (2013.01); *A61B 17/3423* (2013.01); *A61B 17/3498* (2013.01); *A61F 2/4601* (2013.01)

(58) Field of Classification Search
CPC ............ A61B 17/3462; A61B 17/3423; A61B 17/3498; A61B 2017/345;

(Continued)

(56) References Cited

U.S. PATENT DOCUMENTS

| 4,653,477 A | 3/1987 | Akui et al. |
| 4,655,752 A | 4/1987 | Honkanen et al. |

(Continued)

FOREIGN PATENT DOCUMENTS

| CN | 115379876 A | 11/2022 |
| EP | 4103259 A1 | 12/2022 |

(Continued)

OTHER PUBLICATIONS

"U.S. Appl. No. 17/173,531, Advisory Action mailed Apr. 6, 2022", 3 pgs.

(Continued)

*Primary Examiner* — Darwin P Erezo
*Assistant Examiner* — Brigid K Byrd
(74) *Attorney, Agent, or Firm* — SCHWEGMAN LUNDBERG & WOESSNER, P.A.

(57) ABSTRACT

A surgical cannula includes a seal structure including a one-way check valve and a cannula body. The cannula body includes an insertion portion having a distal opening that is configured to be inserted into tissue, and a receiving portion that includes a proximal opening and is configured to reversibly receive the seal structure. In addition, the seal structure is configured to removably associate with the proximal opening of the cannula body, retain a positive pressure within the cannula body when engaged with the cannula body, and retain a positive pressure within the cannula body when an object is inserted through the cannula and the seal structure. Also, the cannula further includes one or more suture attachment structures extending outward laterally from the cannula body; and one or more internal recesses in an inner wall of the cannula located directly adjacent to the one or more suture attachment structures.

8 Claims, 29 Drawing Sheets

Related U.S. Application Data

(60) Provisional application No. 62/972,897, filed on Feb. 11, 2020.

(58) Field of Classification Search
CPC .... A61B 2017/3445; A61B 2017/3433; A61B 17/3417; A61B 17/3415; A61F 2/4601
See application file for complete search history.

(56) References Cited

U.S. PATENT DOCUMENTS

| | | | |
|---|---|---|---|
| 5,195,542 A | 3/1993 | Gazielly et al. | |
| 5,209,736 A | 5/1993 | Stephens et al. | |
| 5,318,589 A | 6/1994 | Lichtman | |
| 5,437,646 A | 8/1995 | Hunt et al. | |
| 5,441,508 A | 8/1995 | Gazielly et al. | |
| 5,512,052 A * | 4/1996 | Jesch | A61M 25/0637 604/164.13 |
| 5,683,378 A | 11/1997 | Christy | |
| 5,792,112 A | 8/1998 | Hart et al. | |
| 5,792,113 A | 8/1998 | Kramer et al. | |
| 6,179,872 B1 | 1/2001 | Bell | |
| 6,755,863 B2 | 6/2004 | Ferree | |
| 6,852,330 B2 | 2/2005 | Bowman et al. | |
| 7,153,312 B1 | 12/2006 | Torrie et al. | |
| 7,559,941 B2 | 7/2009 | Zannis et al. | |
| 7,601,165 B2 | 10/2009 | Stone | |
| 7,658,751 B2 | 2/2010 | Stone et al. | |
| 7,704,263 B2 * | 4/2010 | Morris | A61B 17/0469 606/139 |
| 7,749,250 B2 | 7/2010 | Stone et al. | |
| 7,803,395 B2 | 9/2010 | Datta et al. | |
| 7,819,918 B2 | 10/2010 | Malaviya et al. | |
| 7,887,551 B2 | 2/2011 | Bojarski et al. | |
| 7,909,851 B2 | 3/2011 | Stone et al. | |
| 7,963,972 B2 | 6/2011 | Foerster et al. | |
| 8,080,260 B2 | 12/2011 | Derwin et al. | |
| 8,084,428 B2 | 12/2011 | Spector et al. | |
| 8,088,130 B2 | 1/2012 | Kaiser et al. | |
| 8,092,529 B2 | 1/2012 | Malaviya et al. | |
| 8,118,836 B2 | 2/2012 | Denham et al. | |
| 8,128,658 B2 | 3/2012 | Kaiser et al. | |
| 8,361,113 B2 | 1/2013 | Stone et al. | |
| 8,585,773 B1 | 11/2013 | Kucklick | |
| 8,668,718 B2 | 3/2014 | Euteneuer et al. | |
| 8,753,359 B2 | 6/2014 | Levin et al. | |
| 8,763,878 B2 | 7/2014 | Euteneuer et al. | |
| 8,821,507 B2 | 9/2014 | Axelson, Jr. et al. | |
| 8,821,536 B2 | 9/2014 | Euteneuer et al. | |
| 8,821,537 B2 | 9/2014 | Euteneuer et al. | |
| 8,840,642 B2 | 9/2014 | Euteneuer et al. | |
| 8,864,780 B2 | 10/2014 | Euteneuer et al. | |
| 8,888,811 B2 | 11/2014 | Levin et al. | |
| 8,906,045 B2 | 12/2014 | Levin et al. | |
| 8,920,464 B2 | 12/2014 | Euteneuer et al. | |
| 9,005,224 B2 | 4/2015 | Euteneuer et al. | |
| 9,027,819 B2 | 5/2015 | Euteneuer et al. | |
| 9,033,201 B2 | 5/2015 | Euteneuer | |
| 9,095,337 B2 | 8/2015 | Euteneuer et al. | |
| 9,101,460 B2 | 8/2015 | Euteneuer et al. | |
| 9,107,726 B2 | 8/2015 | Levin et al. | |
| 9,113,977 B2 | 8/2015 | Euteneuer et al. | |
| 9,179,910 B2 | 11/2015 | Euteneuer et al. | |
| 9,179,961 B2 | 11/2015 | Euteneuer et al. | |
| 9,198,750 B2 | 12/2015 | Van Kampen et al. | |
| 9,198,751 B2 | 12/2015 | Euteneuer et al. | |
| 9,204,940 B2 | 12/2015 | Euteneuer et al. | |
| 9,259,220 B2 | 2/2016 | Euteneuer et al. | |
| 9,314,331 B2 | 4/2016 | Euteneuer et al. | |
| 9,393,002 B2 | 7/2016 | Iceman et al. | |
| 9,393,103 B2 | 7/2016 | Van Kampen et al. | |
| 9,393,104 B2 | 7/2016 | Kampen et al. | |
| 9,642,891 B2 | 5/2017 | Hart et al. | |
| 9,655,709 B2 | 5/2017 | Kelly et al. | |
| 9,675,346 B2 | 6/2017 | Euteneuer et al. | |
| 9,743,970 B2 | 8/2017 | Euteneuer et al. | |
| 9,878,141 B2 | 1/2018 | Kucklick | |
| 9,931,119 B2 | 4/2018 | Euteneuer et al. | |
| 9,993,247 B2 | 6/2018 | Euteneuer | |
| 10,085,785 B2 | 10/2018 | Euteneuer et al. | |
| 10,105,210 B2 | 10/2018 | Van Kampen et al. | |
| 10,123,866 B2 | 11/2018 | Van Kampen et al. | |
| 10,172,703 B2 | 1/2019 | Adams et al. | |
| 10,195,016 B2 | 2/2019 | Euteneuer et al. | |
| 10,226,325 B2 | 3/2019 | Euteneuer et al. | |
| 10,245,138 B2 | 4/2019 | Euteneuer et al. | |
| 10,258,459 B2 | 4/2019 | Zenz-Olson | |
| 10,265,156 B2 | 4/2019 | Van Kampen | |
| 10,278,801 B2 | 5/2019 | Kucklick | |
| 10,307,238 B2 | 6/2019 | Kucklick | |
| 10,314,689 B2 | 6/2019 | Zenz-Olson et al. | |
| 10,376,352 B2 | 8/2019 | Kelly et al. | |
| 10,413,397 B2 | 9/2019 | Euteneuer et al. | |
| 10,426,464 B2 | 10/2019 | Euteneuer et al. | |
| 10,449,031 B2 | 10/2019 | Euteneuer et al. | |
| 10,568,622 B2 | 2/2020 | Euteneuer et al. | |
| 10,653,415 B2 | 5/2020 | Euteneuer et al. | |
| 10,675,016 B2 | 6/2020 | Coleman | |
| 10,695,155 B2 | 6/2020 | Levin et al. | |
| 10,765,423 B2 | 9/2020 | Coleman | |
| 10,806,565 B2 | 10/2020 | Euteneuer et al. | |
| 10,813,742 B2 | 10/2020 | Adams et al. | |
| 10,820,981 B2 | 11/2020 | Ravenscroft et al. | |
| 10,835,235 B2 | 11/2020 | Coleman | |
| 10,835,368 B2 | 11/2020 | Zenz-Olson et al. | |
| 10,864,072 B2 | 12/2020 | Van Kampen et al. | |
| 10,874,503 B2 | 12/2020 | Zenz-Olson et al. | |
| 11,559,330 B2 | 1/2023 | Jones et al. | |
| 2002/0127265 A1 | 9/2002 | Bowman et al. | |
| 2005/0113938 A1 | 5/2005 | Jamiolkowski et al. | |
| 2006/0020281 A1 | 1/2006 | Smith | |
| 2006/0029633 A1 | 2/2006 | Kaiser et al. | |
| 2006/0217665 A1 | 9/2006 | Prosek | |
| 2006/0247641 A1 | 11/2006 | Re et al. | |
| 2006/0253077 A1 | 11/2006 | Smith | |
| 2007/0156174 A1 | 7/2007 | Kaiser et al. | |
| 2007/0190108 A1 | 8/2007 | Datta et al. | |
| 2007/0288023 A1 | 12/2007 | Pellegrino et al. | |
| 2008/0051809 A1 | 2/2008 | Verhelst et al. | |
| 2009/0156986 A1 | 6/2009 | Trenhaile | |
| 2009/0156997 A1 | 6/2009 | Trenhaile | |
| 2009/0209915 A1 * | 8/2009 | Zastawny | A61B 17/3462 604/167.02 |
| 2010/0076381 A1 | 3/2010 | Simonsen | |
| 2010/0130939 A1 | 5/2010 | Voss | |
| 2010/0191332 A1 | 7/2010 | Euteneuer et al. | |
| 2011/0087075 A1 | 4/2011 | Wenchell et al. | |
| 2012/0265219 A1 | 10/2012 | Rushdy et al. | |
| 2013/0184716 A1 | 7/2013 | Euteneuer et al. | |
| 2015/0065808 A1 | 3/2015 | Van Wyk et al. | |
| 2015/0327975 A1 | 11/2015 | Euteneuer et al. | |
| 2016/0256254 A1 | 9/2016 | Kucklick | |
| 2017/0072129 A1 | 3/2017 | Slager et al. | |
| 2017/0095269 A1 | 4/2017 | Reid et al. | |
| 2017/0202920 A1 | 7/2017 | Hart et al. | |
| 2018/0116692 A1 | 5/2018 | Mcginley et al. | |
| 2018/0256162 A1 | 9/2018 | Euteneuer | |
| 2018/0271508 A1 | 9/2018 | Berti et al. | |
| 2018/0360914 A1 | 12/2018 | Hart et al. | |
| 2019/0015145 A1 | 1/2019 | Euteneuer et al. | |
| 2019/0029802 A1 | 1/2019 | Van Kampen et al. | |
| 2019/0038395 A1 | 2/2019 | Van Kampen | |
| 2019/0110885 A1 | 4/2019 | Zenz-Olson et al. | |
| 2019/0175328 A1 | 6/2019 | Zenz-Olson et al. | |
| 2019/0209287 A1 | 7/2019 | Zenz-Olson | |
| 2019/0254802 A1 | 8/2019 | Kucklick | |
| 2019/0274675 A1 | 9/2019 | Coleman | |
| 2019/0274814 A1 | 9/2019 | Euteneuer et al. | |
| 2019/0282352 A1 | 9/2019 | Kucklick | |
| 2019/0350608 A1 | 11/2019 | Kucklick | |
| 2019/0388215 A1 | 12/2019 | Euteneuer et al. | |
| 2020/0000462 A1 | 1/2020 | Euteneuer et al. | |
| 2020/0170780 A1 | 6/2020 | Euteneuer et al. | |

(56) References Cited

U.S. PATENT DOCUMENTS

| | | |
|---|---|---|
| 2020/0197003 A1 | 6/2020 | Euteneuer et al. |
| 2020/0237499 A1 | 7/2020 | Zenz-Olson et al. |
| 2021/0275220 A1 | 9/2021 | Jones et al. |

FOREIGN PATENT DOCUMENTS

| | | |
|---|---|---|
| FR | 2800595 B1 | 1/2002 |
| JP | H0698856 B2 | 12/1994 |
| JP | 2023514193 A | 4/2023 |
| WO | WO-2019121987 A1 | 6/2019 |
| WO | WO-2021163317 A1 | 8/2021 |

OTHER PUBLICATIONS

"U.S. Appl. No. 17/173,531, Examiner Interview Summary mailed Mar. 18, 2022", 2 pgs.

"U.S. Appl. No. 17/173,531, Examiner Interview Summary mailed Aug. 22, 2022", 2 pgs.

"U.S. Appl. No. 17/173,531, Examiner Interview Summary mailed Dec. 29, 2021", 2 pgs.

"U.S. Appl. No. 17/173,531, Final Office Action mailed Jan. 25, 2022", 19 pgs.

"U.S. Appl. No. 17/173,531, Non Final Office Action mailed May 17, 2022", 28 pgs.

"U.S. Appl. No. 17/173,531, Non Final Office Action mailed Sep. 23, 2021", 14 pgs.

"U.S. Appl. No. 17/173,531, Notice of Allowance mailed Sep. 15, 2022", 10 pgs.

"U.S. Appl. No. 17/173,531, Notice of Allowance mailed Dec. 27, 2022", 2 pgs.

"U.S. Appl. No. 17/173,531, Response filed Mar. 25, 2022 to Final Office Action mailed Jan. 25, 2022", 14 pgs.

"U.S. Appl. No. 17/173,531, Response filed Aug. 17, 2022 to Non Final Office Action mailed May 17, 2022", 14 pgs.

"U.S. Appl. No. 17/173,531, Response filed Sep. 7, 2021 to Restriction Requirement mailed Jul. 7, 2021", 9 pgs.

"U.S. Appl. No. 17/173,531, Response filed Dec. 22, 2021 to Non Final Office Action mailed Sep. 31, 2021", 12 pgs.

"U.S. Appl. No. 17/173,531, Restriction Requirement mailed Jul. 7, 2021", 6 pgs.

"Australian Application Serial No. 2021219724, First Examination Report mailed Sep. 11, 2023", 4 pgs.

"Brochure—Arthrex Gemini and Twist-in Cannulas", (2012), 8 pgs.

"Brochure—Arthrex PassPort Button Cannula", Arthrex, 2011., (2011), 6 pgs.

"Canadian Application Serial No. 3,170,124, Examiners Rule 86(2) Report mailed Oct. 13, 2023", 3 pgs.

"Chinese Application Serial No. 202180017559.3, Office Action mailed Jun. 7, 2023", w/ English translation, 23 pgs.

"International Application Serial No. PCT/US2021/017648, International Preliminary Report on Patentability mailed Aug. 25, 2022", 10 pgs.

"International Application Serial No. PCT/US2021/017648, International Search Report mailed May 13, 2021", 2 pgs.

"International Application Serial No. PCT/US2021/017648, Written Opinion mailed May 13, 2021", 8 pgs.

"Japanese Application Serial No. 2022-548554, Notification of Reasons for Refusal mailed Sep. 14, 2023", w/ English Translation, 9 pgs.

"Japanese Application Serial No. 2022-548554, Written Amendment filed Dec. 1, 2022", w/ English Translation, 7 pgs.

"Rotator Cuff Failure, UW Orthopaedics and Sports Medicine, Seattle", [Online]. Retrieved from the Internet: <URL: https://orthop.washington.edu/patient-care/articles/shoulder/rotator-cuff-failure.Html>, (Jan. 25, 2005), 11 pgs.

* cited by examiner

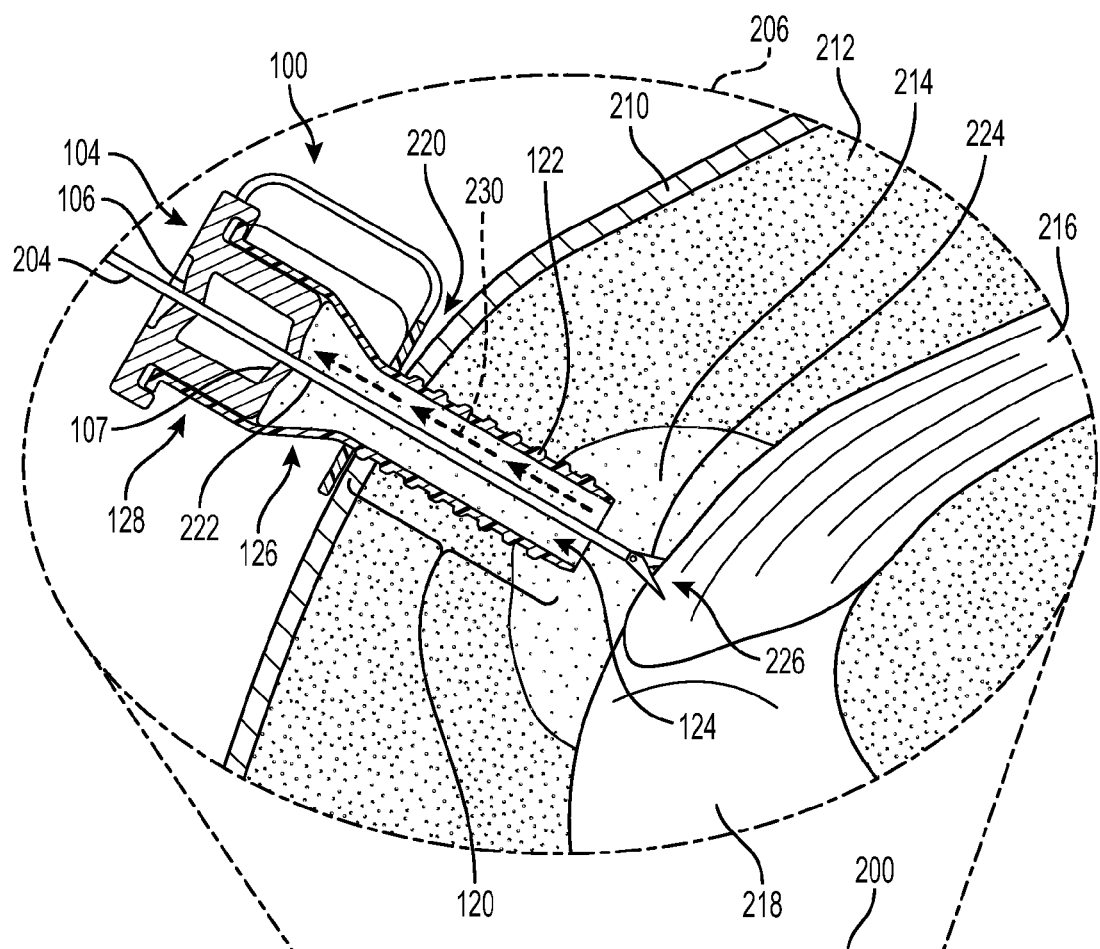
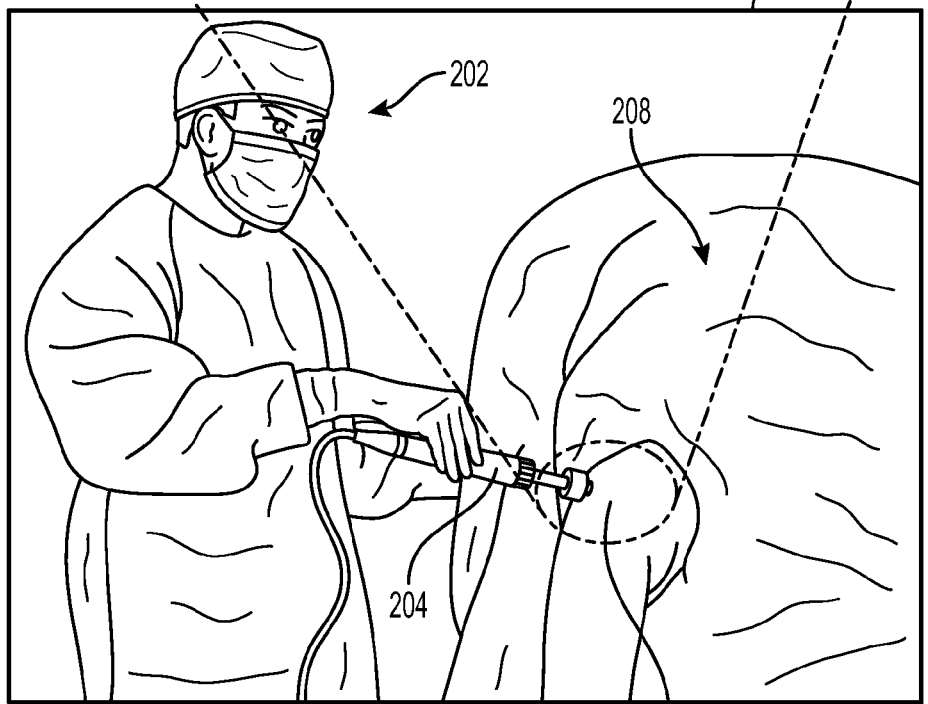
FIG. 4

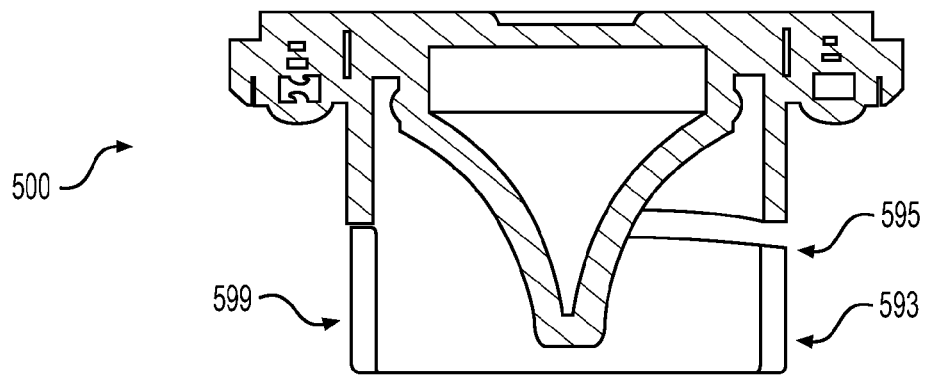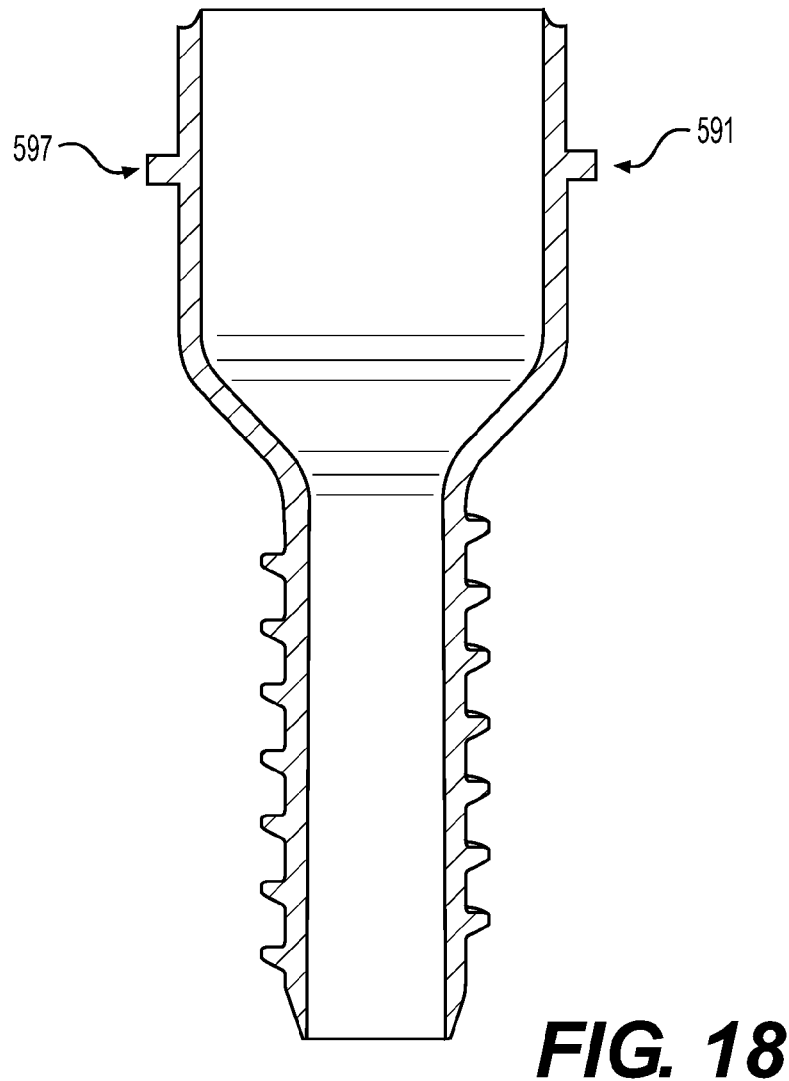
FIG. 18

SURGICAL CANNULA WITH REMOVABLE PRESSURE SEAL

CROSS-CITATION OF RELATED APPLICATIONS

This application is a continuation of U.S. patent application Ser. No. 17/173,531, filed Feb. 11, 2021, and entitled "Surgical Cannula with Removable Pressure Seal," which claims priority to U.S. Provisional Application No. 62/972,897, filed Feb. 11, 2020, and entitled "Cannula with Removable Pressure Seal." The entire disclosure of each of the applications mentioned above is incorporated herein by reference.

TECHNICAL FIELD

The present disclosure relates to the field of surgical cannulas that may be temporarily inserted into living tissue. Cannulas may be used during surgery to introduce tools or substrates into a human or animal body.

BACKGROUND

Surgical cannulas are generally well-known in the art of arthroscopic surgery. For example, various types of cannulas are used to control the inflow or outflow of fluids, to allow access for tools into the tissue, and for other functions. In some types of surgeries, a graft or other substrate material may be introduced into a surgical site. Additionally, many arthroscopic surgeries, such as joint surgeries, use pressurized irrigation fluid to keep tissue separated apart from other tissue. In particular, pressurized irrigation fluid may be used to aid in visualization of the surgical site as well as to prevent bleeding from vasculature surrounding the surgical cuts. Other types of surgeries, such as gastrointestinal procedures, use pressurized gas to provide access to and visualization of the surgical site.

Accordingly, there is a need in the art for cannulas that address the need to serve these several functions during an arthroscopic surgery.

SUMMARY OF THE DISCLOSURE

In one aspect, the disclosure provides a surgical cannula comprising: a seal structure including at least one valve; and a cannula body, including: an insertion portion having a distal opening that is configured to be inserted into tissue, and a receiving portion that includes a proximal opening and is configured to reversibly receive the seal structure; wherein the seal structure is configured to removably associate with the proximal opening of the cannula body; and wherein the seal structure is configured to retain a positive pressure within the cannula body when engaged with the cannula body, and the seal structure is configured to retain a positive pressure within the cannula body when an object is inserted through the cannula and the seal structure.

In another aspect, the disclosure provides a surgical cannula comprising: a seal structure including a first valve and a second valve; and a cannula body, including: an insertion portion that includes a distal opening and is configured to be inserted into tissue, and a receiving portion that includes a proximal opening and is configured to reversibly receive the seal structure; wherein the seal structure reversibly covers the proximal opening of the cannula body; wherein the seal structure is configured to retain a positive pressure within the cannula body when an object is inserted through the cannula.

In another aspect, this disclosure provides a surgical cannula comprising: a seal structure including at least one valve; and a cannula body, including an insertion portion that includes a distal opening and is configured to be inserted into tissue, and a receiving portion that includes a proximal opening and is configured to reversibly receive the seal structure; wherein the seal structure is configured to retain a positive pressure within the cannula body when an object is inserted through the cannula and the seal structure; and wherein the cannula body further includes one or more suture attachment structures configured to hold a suture so as to anchor the cannula to tissue into which the insertion portion has been inserted.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 4 is a cross-sectional view of a first surgical procedure that involves the use of a surgical cannula in accordance with this disclosure;

FIG. 18 is a cross-sectional view of the third embodiment of a surgical cannula in accordance with this disclosure;

DETAILED DESCRIPTION

Broadly disclosed are surgical cannulas that include a removable seal structure that retains pressure inside the cannula. Such a cannula may be used during arthroscopic surgery to both provide an inlet for arthroscopic tools, and also act as a port to allow introduction of a graft substrate into the surgical site.

Generally, a cannula may broadly refer to a tube that can be inserted into the body, and used for the delivery or extraction of fluid or other materials. Surgical cannulas may generally include intravenous cannulas, nasal cannulas, or surgical cannulas.

In particular, this disclosure is directed to surgical cannulas that may retain pressurized fluid (liquid or gas) within a surgical site when a seal structure is engaged on the cannula, while also allowing removal of the seal structure in order to permit larger items, such as tissue grafts, to be introduced through the cannula.

Figure 1:
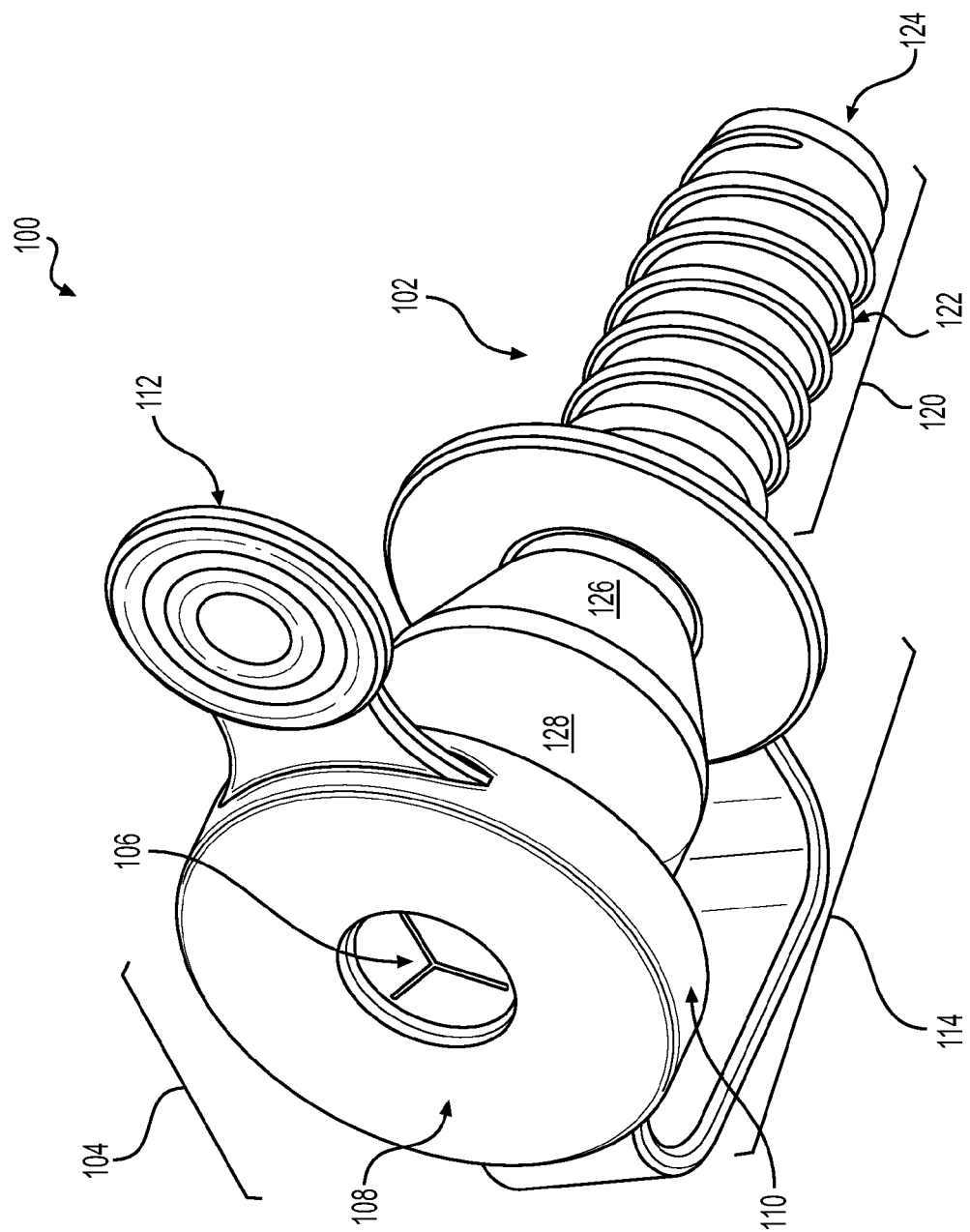
FIG. 1 is a perspective top view of a first embodiment of a surgical cannula in accordance with this disclosure.

For example, FIG. 1 shows a first embodiment of a cannula in accordance with this disclosure. Cannula 100 may include cannula body portion 102 that includes an insertion portion 120, a receiving portion 128, and a taper portion 126 between the two. Insertion portion 120 may include a distal opening 124 in the cannula. Insertion portion 120 may be configured to be inserted into tissue, such as a human body or an animal body, and may be generally cylindrical in shape. Insertion portion 120 may also include threads 122 on an exterior surface thereof.

Threads 122 may secure cannula 100 in the tissue, and may allow more accurate placement of the cannula 100 within the tissue by allowing a user to increase or decrease the depth to which the cannula is inserted into the tissue by rotating the cannula 100.

Cannula 100 may also include a seal structure 104. Seal structure 104 may engage with receiving portion 128. Seal structure 104 may include a valve 106. In some embodiments, valve 106 may be a tricuspid valve, as shown in FIG. 1. A tricuspid valve, as is generally known in the art, is a one-way valve made up of three flaps that come together at a single point. Valve 106 may therefore retain fluidic pressure inside cannula body 102 when cannula 100 is used in a surgical procedure.

Seal structure 104 may also include top portion 108 and side portion 110. Finally, seal structure 104 may also include tether 114 that may connect seal structure 104 to cannula body portion 102 when seal structure is not engaged with receiving portion 128.

Figure 2:
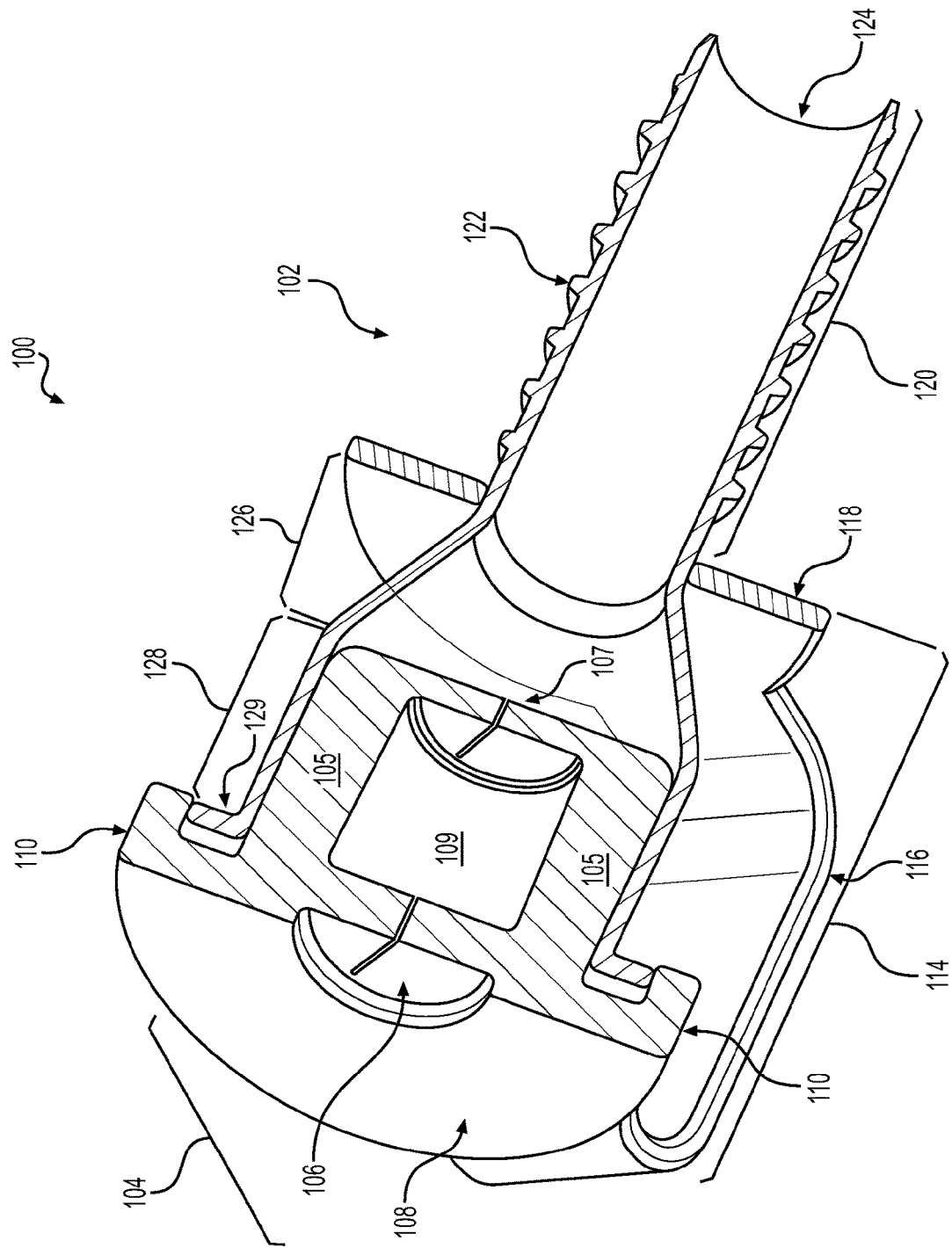
FIG. 2 is a perspective cross-sectional view of the first embodiment of a surgical cannula in accordance with this disclosure.

FIG. 2 shows cannula 100 in further detail. FIG. 2 shows a cross-sectional view of cannula 100. As shown in this view, cannula body 102 may be hollow so as to allow passage of tools or tissue through the cannula 100 from a proximal end to a distal end 124. Namely, insertion portion 120 of cannula body 102 may be a hollow cylinder of a first gauge (diameter), receiving portion 128 of cannula body 102 may be a hollow cylinder of a second gauge (diameter) that is larger than the first gauge, and taper portion 126 may taper in gauge between the two.

Seal structure 104 may also include side portion 110 that engages with lip 129 on cannula body portion 102 to engage a seal between seal structure 104 and cannula body portion 102. Lip 129 may cause seal structure 104 to be securely, but reversibly, retained against cannula body portion 102.

In the embodiment shown in FIG. 2, seal structure 104 may include first valve 106 and also second valve 107. The use of two such valves may even better ensure that pressure is retained inside cannula 100 during surgical use. In some embodiments, first valve 106 may be a tricuspid valve and second valve 107 may also be a tricuspid valve, as shown in FIG. 2. In some embodiments, other types of valves may be used. Other embodiments discussed herein utilize duckbill valves. In some cases, such a duckbill valve may be utilized in the embodiment shown in FIGS. 1-7 (e.g., substituted for one or both of the tricuspid valves).

First valve 106 and second valve 107 may be separated by a void 109 defined by seal sidewalls 105. Void 109 may catch any seepage of a pressurized fluid from taper portion 126 and insertion portion 120 that escapes past second valve 107, while first valve 106 may still ensure no liquid escapes to outside of the cannula.

FIG. 2 also shows tether 114 in greater detail. Namely, tether 114 may include arm portion 116 that connects to top portion 108 of seal structure 104 at one end of arm portion 116. Arm portion 116 may then connect to ring portion 118 that encircles one end of insertion portion 120 of the cannula body 102. In this way, tether 114 may connect seal structure 104 to cannula body portion 102 even when seal structure 104 is not engaged with receiving portion 126.

Also as shown in FIG. 2, seal structure 104 may be a continuous unitary piece of a single material. In some embodiments, seal structure 104 may be made of continuous silicone material.

Figure 3:
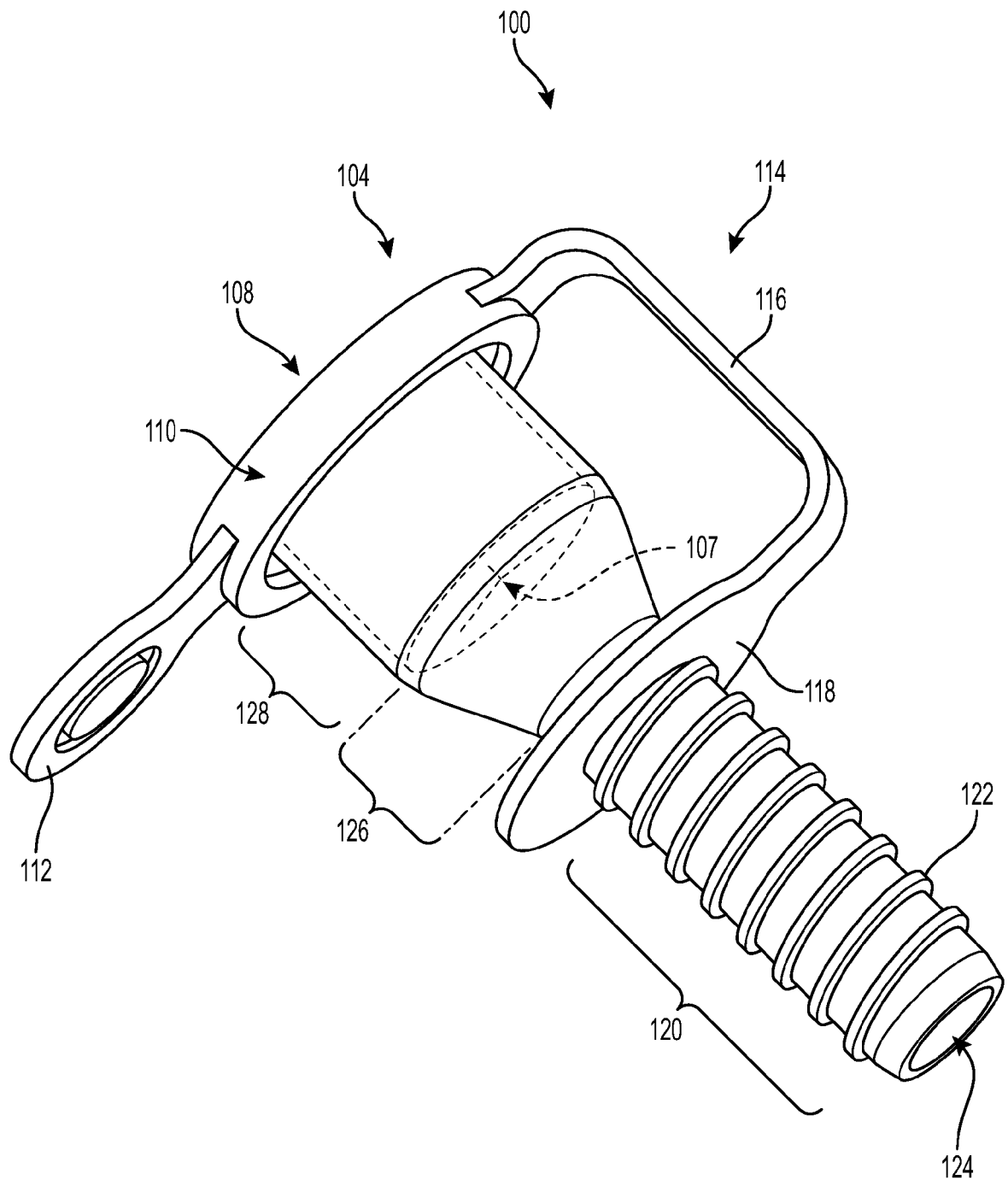
FIG. 3 is a perspective bottom view of the first embodiment of a surgical cannula in accordance with this disclosure.

FIG. 3 shows cannula 100 from a perspective bottom view. In this view, FIG. 3 shows how cannula 100 looks when seal structure 104 is engaged with receiving portion 128. Namely, second valve 107 is adjacent to taper portion 126 so as to retain any pressurized fluid within a surgical site that may flow upward into insertion portion 120 and taper portion 126.

Also shown in FIG. 3 is tab portion 112 that may be connected to side portion 110 of top portion 108 of seal structure 104. Tab portion 112 may allow a user to easily and conveniently remove seal structure 104 from engagement with cannula body portion 102. For example, a surgeon may remove seal structure 104 from cannula body portion 102 by grasping tab 112 and pulling on tab 112 until side portion 110 no longer engages with lip 129 (see FIG. 2 for connection between side portion 110 and lip 129).

FIG. 4 shows one example of how a cannula in accordance with this disclosure may be used during a surgical procedure. In the embodiment shown in FIG. 4, a surgeon 202 may operate a tool 204 that is inserted through cannula 100, which has been inserted into a patient 208 at surgical site 206. Accordingly, this disclosure also provides methods of performing arthroscopic surgery using the cannula devices disclosed herein.

The cross section of surgical site 206 shown in FIG. 4 shows how the cannula is used during a surgical procedure in greater detail. Namely, insertion portion 120 of cannula 100 may be partially implanted into the patient's tissue using threads 122. Cannula 100 may be introduced into the tissue by first making an incision 220 into skin tissue 210 and muscle tissue 212 such that distal end 124 will be located adjacent to the desired surgical site 226. In the embodiment shown, the surgical procedure may be a rotator cuff surgery. In this embodiment, desired surgical site 226 may be where rotator cuff muscle and ligaments 216 attach to the humoral head 218 at the subacromial space.

In order to perform such a surgery, a pressurized liquid 214 may be used to inflate and visualize the surgical site 226. Pressurized liquid 214 may be clear saline, for example. Also referred to as an irrigation fluid, pressurized liquid 214 may be an isotonic solution that is used to enable visualization and also prevent bleeding from vasculature surrounding the surgical site 226. Pressurized liquid 214 may be at a pressure of around 20-30 mmHg. In some cases, debris or blood may cloud the pressurized fluid. In such cases, the pressurized fluid may be flushed. In doing so, the pressure and flow of the fluid may be raised significantly. Accordingly, in order to withstand such elevated pressures, in some embodiments, the disclosed seal of the cannula may be configured to sustain pressures up to about 140 mmHg.

Cannula 100 may allow surgeon 202 to introduce tool 204 into the surgical site 226 while retaining fluid 214 under pressurization. Tool 204 may include tool shaft 222 that extends through cannula 100 and ends at tool tip 224. Namely, tool shaft 222 may extend through first valve 106 and second valve 107 which conform around tool shaft 222 such that pressurization 230 of the pressurized liquid 214 is contained within the surgical site 226 as well as within the insertion portion 120 and taper portion 126 of cannula 100. In this way, seal structure 104 may be configured to retain a positive pressure 230 within the cannula body when a tool 204 is inserted through the cannula 100.

Figure 5:
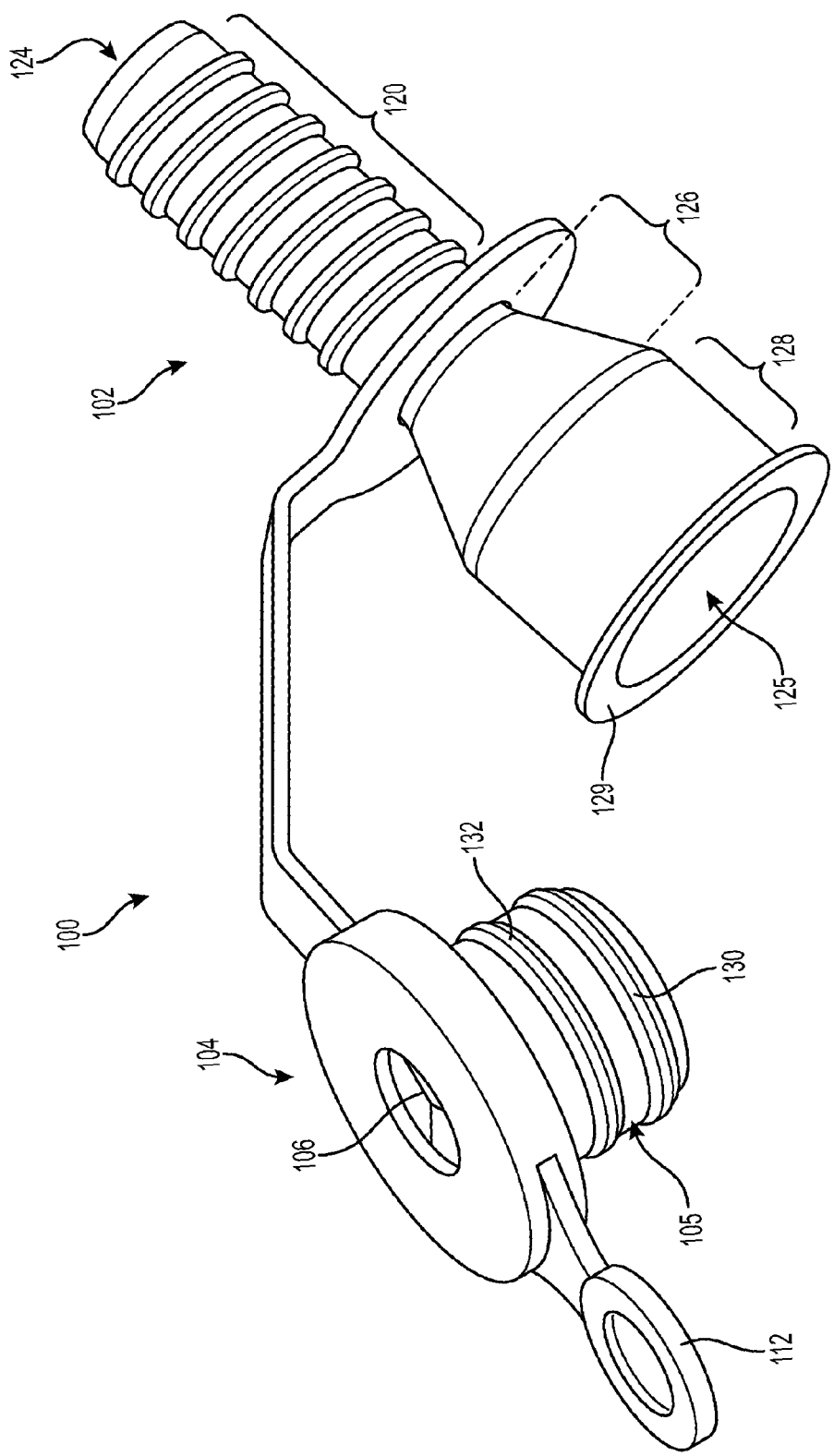
FIG. 5 is a perspective view of the first embodiment of a surgical cannula with the removable top separated from the cannula body.

FIG. 5 next shows cannula 100 when seal structure 104 is not engaged with cannula body portion 102. As mentioned, tether 114 may keep seal structure 104 attached to cannula body portion 102 even when seal structure 104 is not engaged with body portion 102. Also shown in FIG. 5 is proximal opening 125 in receiving portion 128 that is located opposite distal opening 124 in insertion portion 120. Proximal opening 125 may be surrounded by lip 129, which engages with side portion 110 of seal structure 104, as mentioned above. Seal structure 104 may therefore cover proximal opening 125 when seal structure 104 is engaged with cannula body portion 102.

The embodiment in FIG. 5 may also include ridges 130, 132 on seal sidewalls 105 that further ensure a tight (but reversible) fit between seal structure 104 and receiving portion 128. As shown in FIGS. 2, 3, and 5, in this embodiment, seal sidewalls 105 engage with an interior surface of receiving portion 128. Ridges 130, 132 may therefore abut interior surface of receiving portion 128 in order to form a seal that retains pressure.

Figure 6:
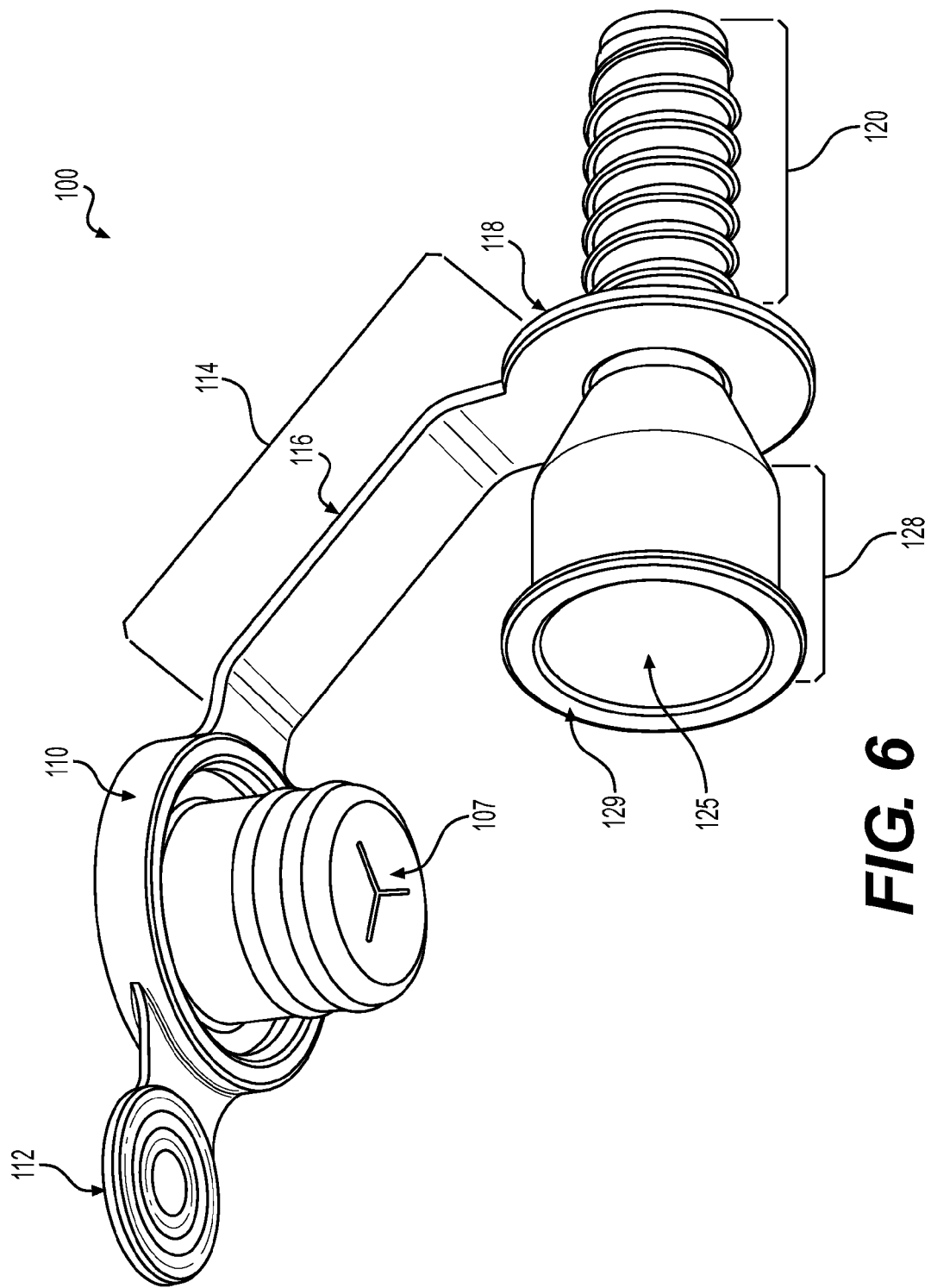
FIG. 6 is another perspective view of the surgical cannula with the removable top separated from the cannula body.

FIG. 6 shows the embodiment of FIG. 5 from another angle, in order to show additional details of seal structure 104. Namely, second valve 107 may be disposed on a bottom side of seal structure 104 such that second valve 107 may be inserted into receiving portion 128 so as to be located at the most distal end of receiving portion 128.

Also shown in FIG. 6 is tether 114. Tether 114 may include arm portion 116 that connects seal structure side portion 110 with ring portion 118. Ring portion 118 may encircle cannula body 104 at a nearest end of insertion portion 120.

Thus, as shown in FIGS. 5 and 6, seal structure 104 may be reversibly engaged with cannula body portion 102 and thus may be removed after engagement with cannula body portion 102.

Figure 7:
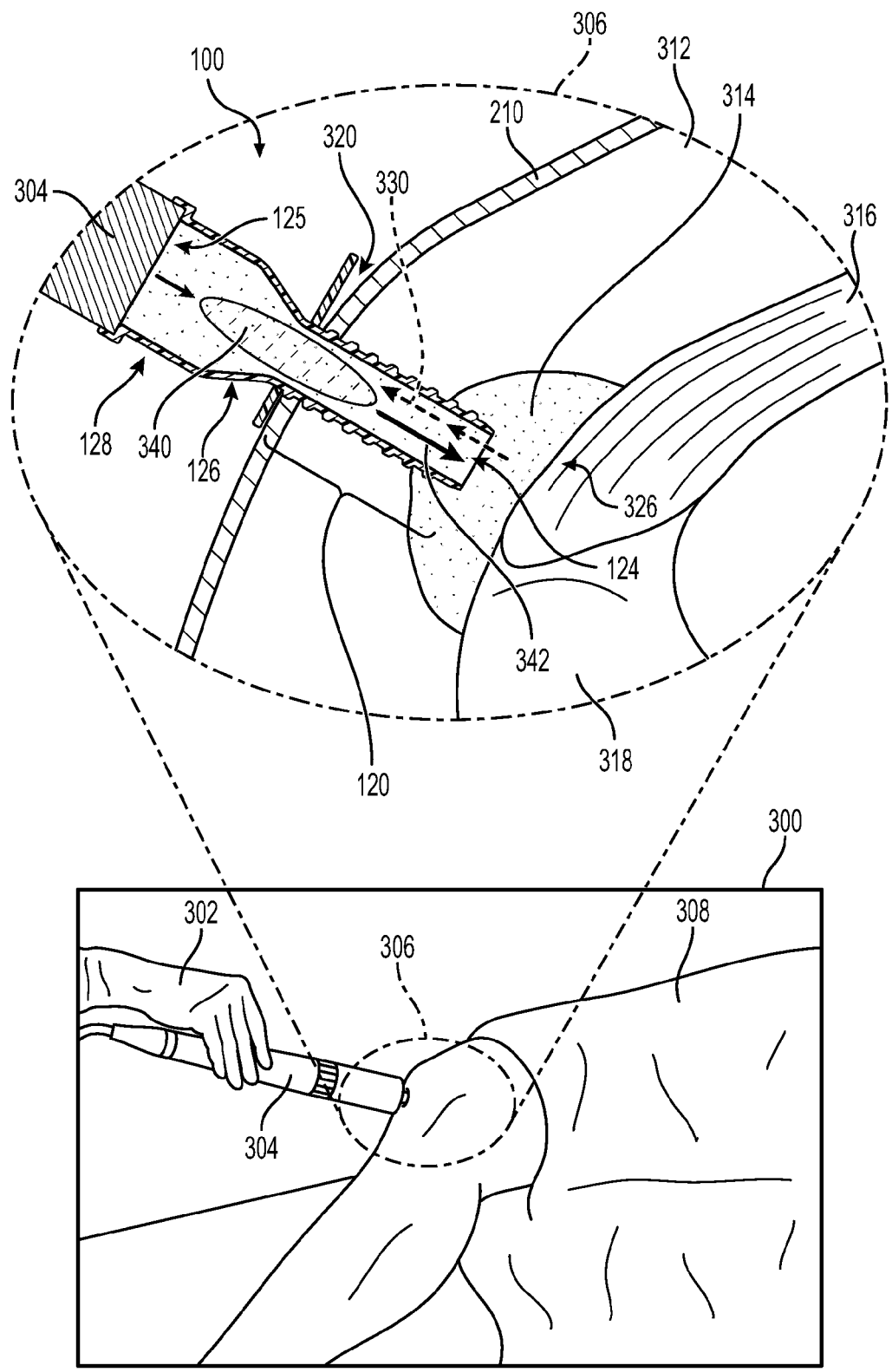
FIG. 7 is a cross-sectional view of a second surgical procedure that involves the use of a surgical cannula in accordance with this disclosure.

FIG. 7 shows another surgical procedure 300, and how cannula 100 may be used when the seal structure is removed from the cannula body portion. Namely, in this embodiment, surgeon 302 may perform surgery on a patient 308 at the patient's knee 306 through an insertion 320 in the patient's skin 210 and through tissue 312 surrounding the surgical site. At the stage of the surgery shown, a graft substrate 340 is ready to be introduced into the surgical site 326. This would typically occur after a surgical site 226/326 has been prepared through one or more steps involving the use of tools at the surgical site as shown in FIG. 4. In this way, a method of performing arthroscopic surgery in accordance with this disclosure may include delivering a sheet-like implant 340 through the cannula 100 to the surgical site, and securing the sheet-like implant 340 to tissue 316 at the surgical site 326.

In the stage of surgery shown in FIG. 7, pressurized liquid 314 is in fluidic communication with the entire interior of cannula 100. Namely, because seal structure 104 has been removed, pressurized liquid 314 may expand up into insertion portion 120, taper portion 126, and receiving portion 128 as shown. Tool 304 may then be attached to proximal opening 125 of cannula 100 and used to introduce graft sheet-life substrate 340 into the interior of the cannula 100 and allow graft substrate 340 to travel down the length of cannula 100 to surgical site 326 along path 342. Tool 304 may include aspects for maintaining pressurized liquid 314 under pressure 330 during this surgical step. For example, tool 304 may include one or more sealing structures on the shaft of tool 304. Such sealing structures may seal the cannula during the insertion of the graft.

In this way, cannula 100 may be configured so as to allow a graft substrate 340 to travel through it. Namely, cannula 100 may be of sufficient size to allow graft substrate 340 to fit therein. The gauge of the various cannula sections may differ depending on the size of the patient and the type of surgery for which it is used. In addition, the relative proportions of the gauges of the different portions of the cannula may differ.

However, in particular embodiments, the second gauge of receiving portion 128 being larger than the first gauge of insertion portion 120 may advantageously help the sheet-like graft substrate 340 (and any supporting structures that may aid in the place of the graft substrate 340) roll itself up as it passes along cannula body portion 102 from proximal opening 125 to distal opening 124. Namely, the shape of taper portion 126 may cause the graft substrate 340 to roll up—and thereby assume a configuration that is advantageous for placement for attachment to the patient's tissue 316t. The relative size of the gauges of the various sections of cannula body portion 102 may therefore advantageously aid in the accomplishment of the purpose for which the cannula 100 is to be used.

Subsequently, after the graft substrate 340 is successfully inserted, seal structure 104 may be re-engaged with cannula body portion. Then, surgical tools may again be introduced into the surgical site (in order to manipulate the graft substrate 340 and attached it where needed) as shown in FIG. 4. In this way, a single surgical cannula 100 may both allow for the introduction of tools into a surgical site under a pressurized liquid, and also allow introduction of a graft substrate into the surgical site.

Figure 8:
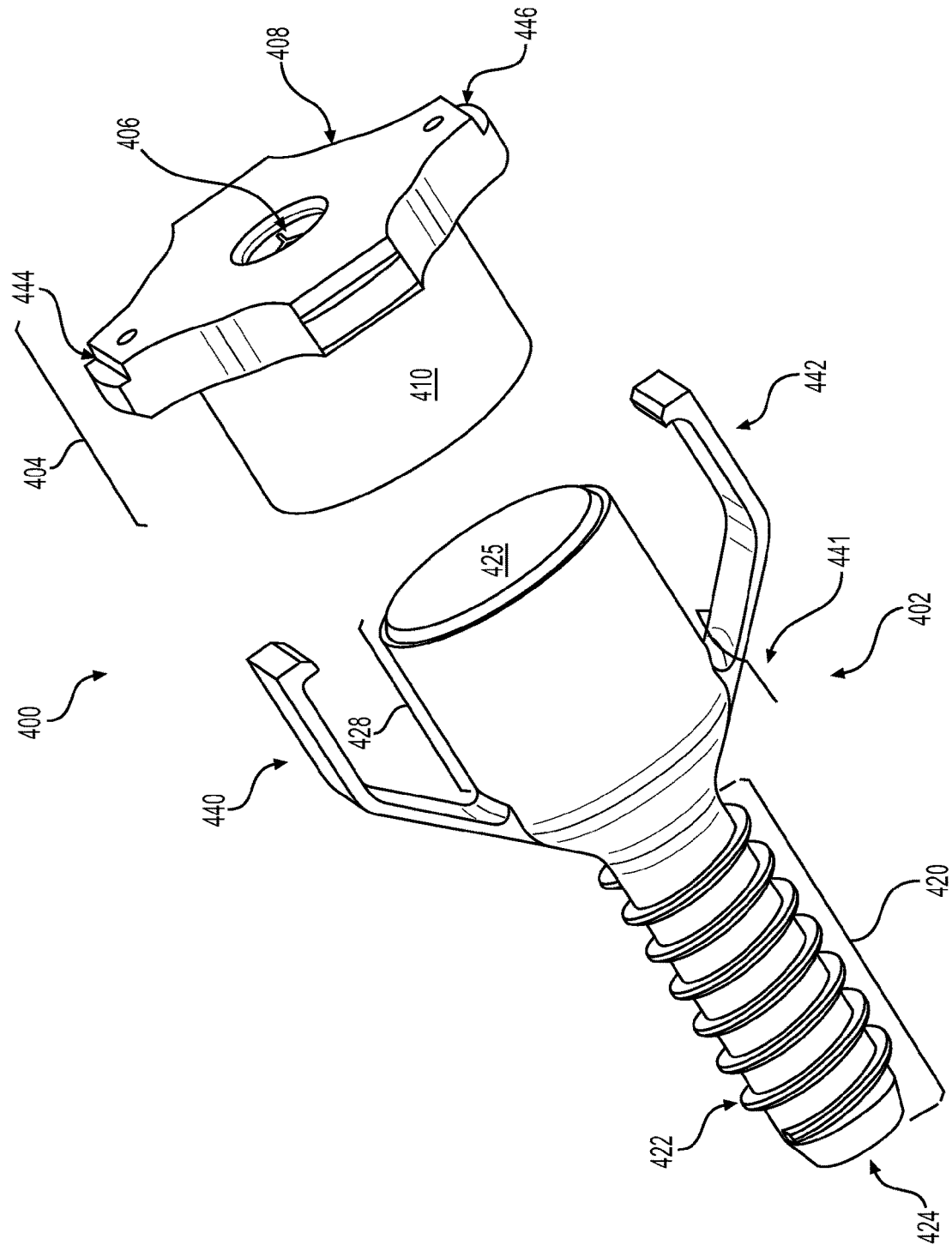
FIG. 8 is a perspective top view of a second embodiment of a surgical cannula in accordance with this disclosure.

FIG. 8 shows a second embodiment of a cannula 400 in accordance with this disclosure. Cannula 400 may include some features that are substantially similar to features in the first embodiment of cannula 100 discussed above. Namely, cannula 400 may include cannula body portion 402 that includes insertion portion 420 and receiving portion 428. Insertion portion 420 may include distal opening 424 and threads 422. Receiving portion 428 may include proximal opening 425. Cannula 400 may also include seal structure 404. Seal structure 404 may include side surface 410, first valve 406, and housing cover 408.

In the particular embodiment shown in FIG. 8, cannula 400 may also include first wing structure 440 and second wing structure 442. Each of first wing structure 440 and second wing structure 442 may extend laterally outward from cannula body 402 and upward so as to latch onto housing cover 408. Namely, housing cover 408 may include first notch 444 that is configured to receive first wing structure 440. Housing cover 408 may also include second notch 446 that is configured to receive second wing structure 442.

Additionally, first wing structure 440 and second wing structure 442 may also act as suture attachment structures. Namely, during surgery a user may choose to anchor cannula 400 to the tissue through which it is inserted by suturing one or more suture attachment structures to the tissue. Namely, sewing a thread of suture 441 around the suture attachment structure and through the tissue such that the suture holds the cannula 400 in place. In this way, a cannula 400 in accordance with this disclosure may include one or more suture attachment structures that may be configured to hold a suture so as to anchor the cannula to the tissue into which the insertion portion 420 of the cannula 400 has been inserted.

Figure 9:
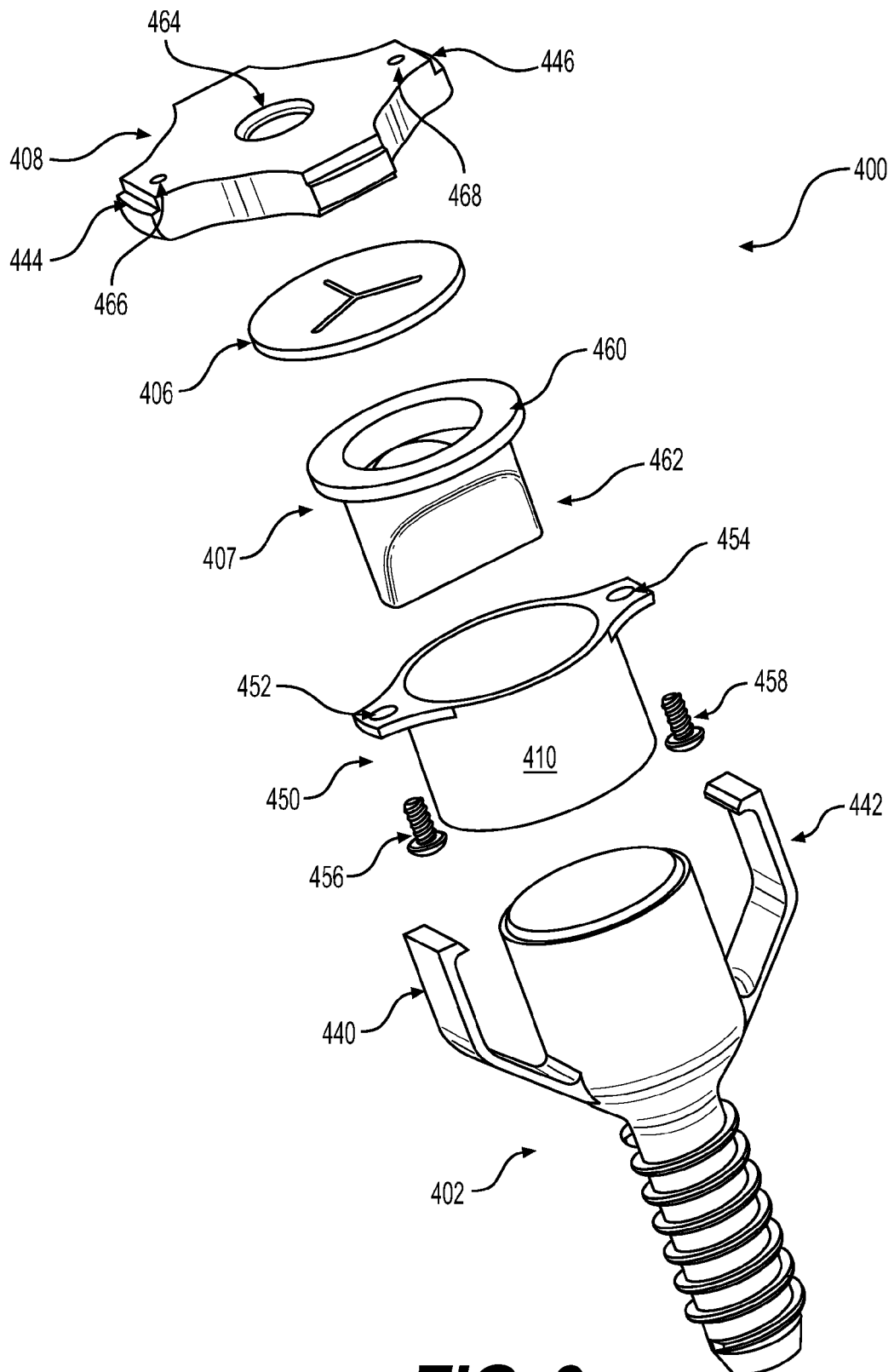
FIG. 9 is an exploded view of the several subcomponents making up the second embodiment of a surgical cannula in accordance with this disclosure.

FIG. 9 shows an exploded view of the several components that may make up cannula 400. Namely, cannula 400 may include: cannula body portion 402 that includes first wing structure 440 and second wing structure 442, lower housing portion 450, a first attachment screw 456, a second attachment screw 458, first valve 406, a second valve 407, and housing cover 408.

In this particular embodiment, lower housing portion 450 may include seal side surface 410, first flange hole 452, and second flange hole 454.

First valve 406 may be a tricuspid valve as discussed with respect to other embodiments above.

Second valve 407 may, in some embodiments, be a duckbill valve. A duckbill valve, as is generally known, is a type of one-way valve that has two "lips" 462 in the shape of a duck's bill that come together to form a seal. Generally, the two lips in a duckbill valve may bend open when pressure is applied from one direction, but not from the other. Duckbill valves may therefore act as a self-contained check valve. Second valve 407 may also include rim portion 460 that may allow second valve 407 to be held in place between lower housing portion 450 and housing cover 408.

Housing cover 408 may include: first cover hole 466, second cover hole 468, first notch 444, second notch 446, and access hole 464. First cover hole 466 and second cover hole 468 may be located on opposite sides of housing cover from each other, as may be first notch 444 and second notch 446. First cover hole 466 may be adjacent to first notch 444, and second cover hole 468 may be adjacent to second notch 446.

Additionally, first attachment screw 456 and second attachment screw 458 may secure lower housing portion 450 to housing cover 408, in such a way that first valve 406 and second valve 407 are contained therein. Namely, first attachment screw 456 may extend through first flange hole 452 on lower housing portion 450 into first cover hole 466 in housing cover 408. Similarly, second attachment screw 458 may extend through second flange hole 454 on lower housing portion 450 into second cover hole 468 in housing cover 408.

In other embodiments, lower housing portion 450 and housing cover 408 may be attached to each other by attachment means other than screws, such as ultrasonic welding or other types of thermal bonding, adhesive, or any other suitable fixation modality.

Figure 10:
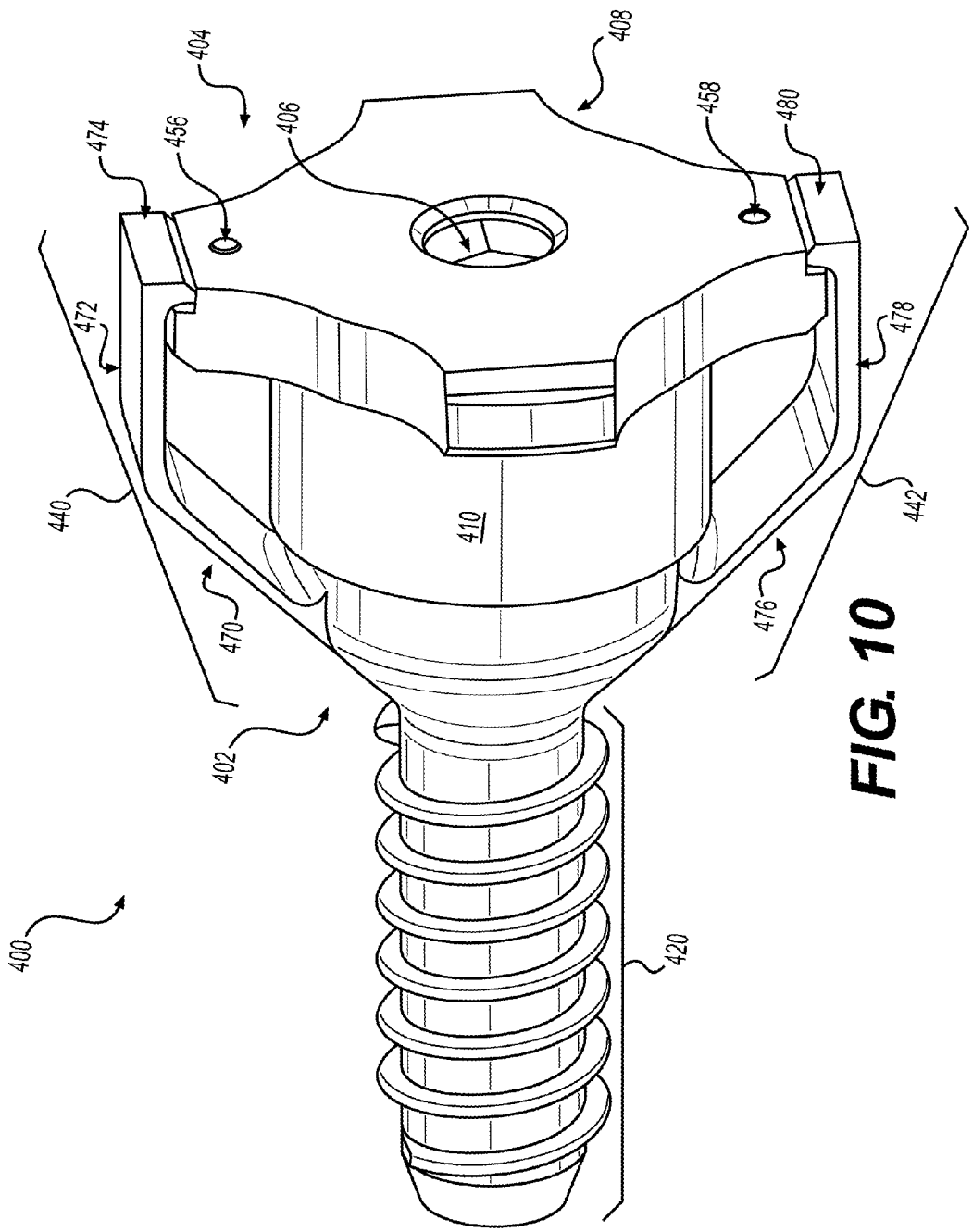
FIG. 10 is a perspective top view of the second embodiment of a surgical cannula with the removable top secured to the cannula.

FIG. 10 shows another view of cannula 400. In this view, seal structure 404 is engaged with cannula body 402. In this configuration, seal structure 404 is latched into place by first wing structure 440 and second wing structure 442. Namely, first wing structure 440 may include first diagonal portion 470 that extends outward from cannula body 402 and upwards towards proximal opening 425 (note: proximal opening 425 is covered by seal structure 404 in FIG. 10), first vertical portion 472 that extends upward toward proximal opening 425, and first latch portion 474 that engages first notch 444 on housing cover 408. Second wing structure 442 may similarly include second diagonal portion 476, second vertical portion 478, and second latch portion 480 that engages with second notch 446 on housing cover 408. First wing structure 440 and second wing structure 442 may be disposed on opposite sides of cannula body 402.

When seal structure 404 is engaged with cannula body 402, side surface 410 may be located on the outside of receiving portion 428 of cannula body 402 and surround it.

Figure 11:
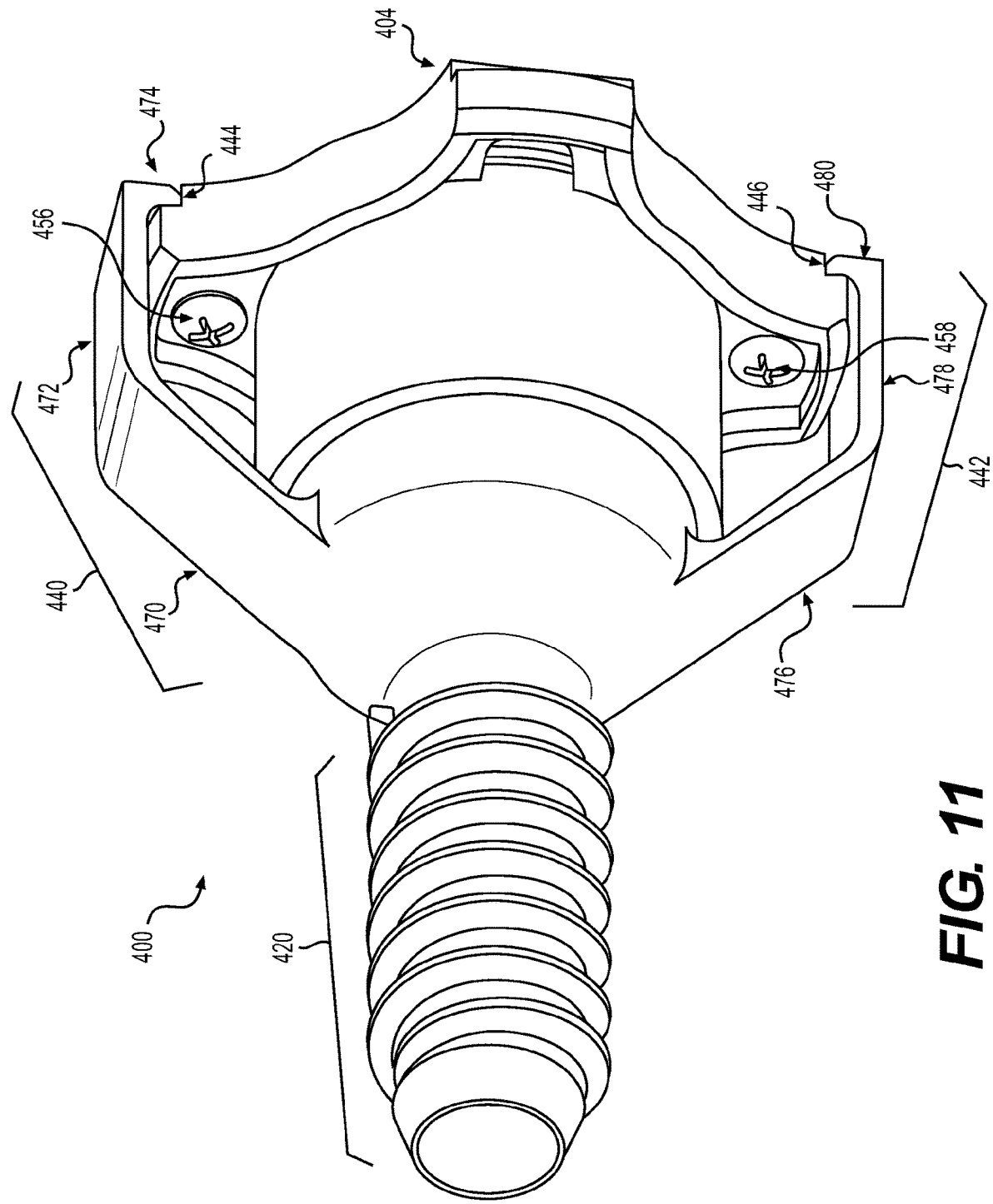
FIG. 11 is a perspective bottom view of the second embodiment of a surgical cannula with the removable top secured to the cannula.

FIG. 11 shows a bottom isometric view of cannula 400 when seal structure 404 is engaged with receiving portion 428 of cannula body 402. This view further shows how first attachment screw 456 and second attachment screw 458 may secure lower housing portion 450 to housing cover 408.

Figure 12:
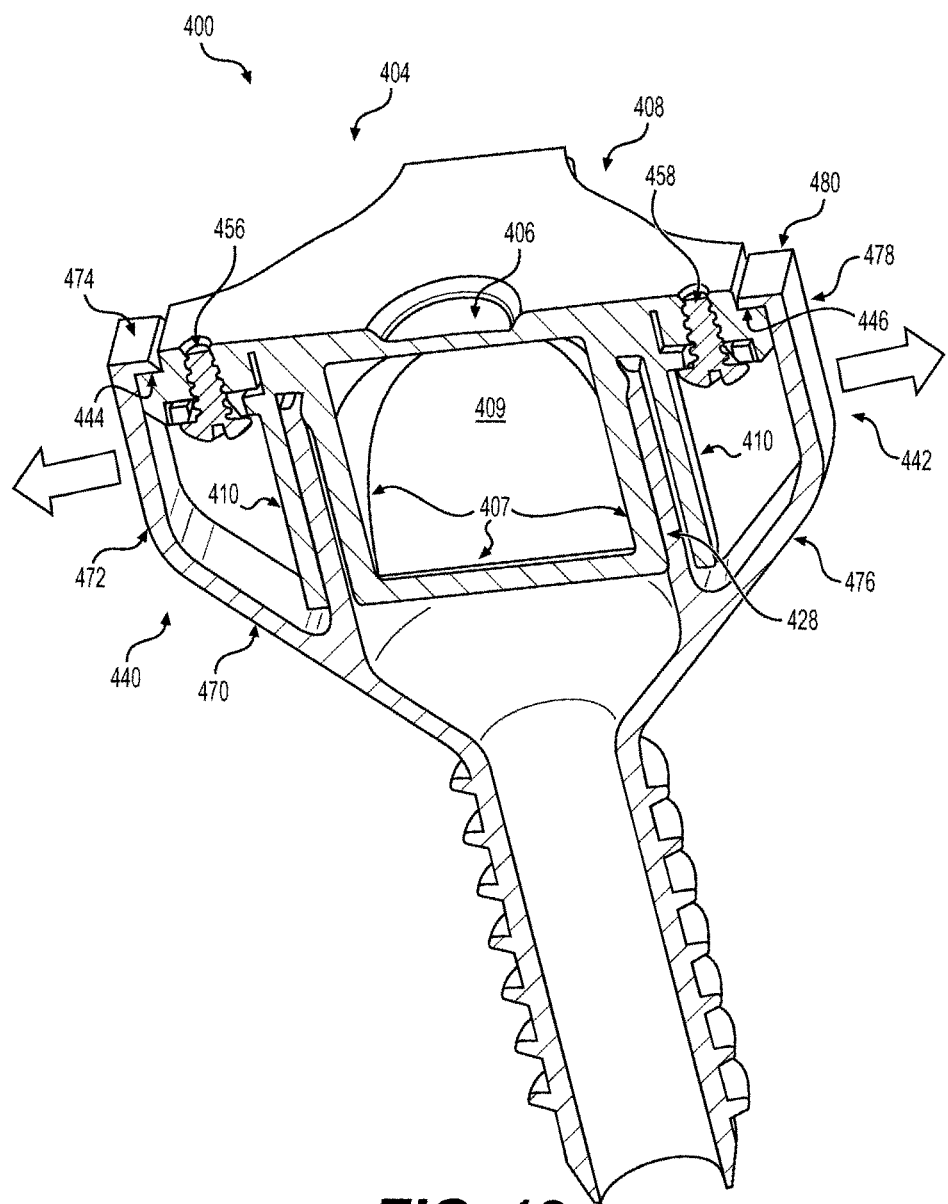
FIG. 12 is a first perspective cross-sectional view of the second embodiment of a surgical cannula in accordance with this disclosure.

FIG. 12 is a cross-sectional view of cannula 400. This cross-sectional view shows additional details of an embodiment where first attachment screw 456 and second attachment screw 458 extend upward through first flange hole 452 and second flange hole 454, and into first cover hole 466 and second cover hole 468. As a result, lower housing portion 450 and housing cover 408 hold first valve 406 and second valve 407 in place. Also shown is void 409 between first valve 406 and second valve 407.

In particular, FIG. 12 further shows how first wing structure 440 and second wing structure 442 reversibly hold seal structure 404 in place. Namely, first wing structure 440 and second wing structure 442 are semi-rigid, and are biased into a position that hold latch portions 474, 480 into notches 444, 446 when seal structure 404 is engaged onto cannula body 402. However, first wing structure 440 and second wing structure 442 may be partially flexible in an outward lateral direction as shown by arrows, that allows latch portions 474, 480 to slide off of notches 444, 446. In this way, seal structure 404 may be disengaged and removed from cannula body 402 in an alternative manner. First wing structure 440 and second wing structure 442 may be configured such that a surgeon may disengage seal structure 404 with an outward motion of a thumb and forefinger, thereby allowing ease of use during surgery. Non-rotational disengagement may be preferred in some situations, for example where an instrument remains inserted through the cannula.

Figure 13:
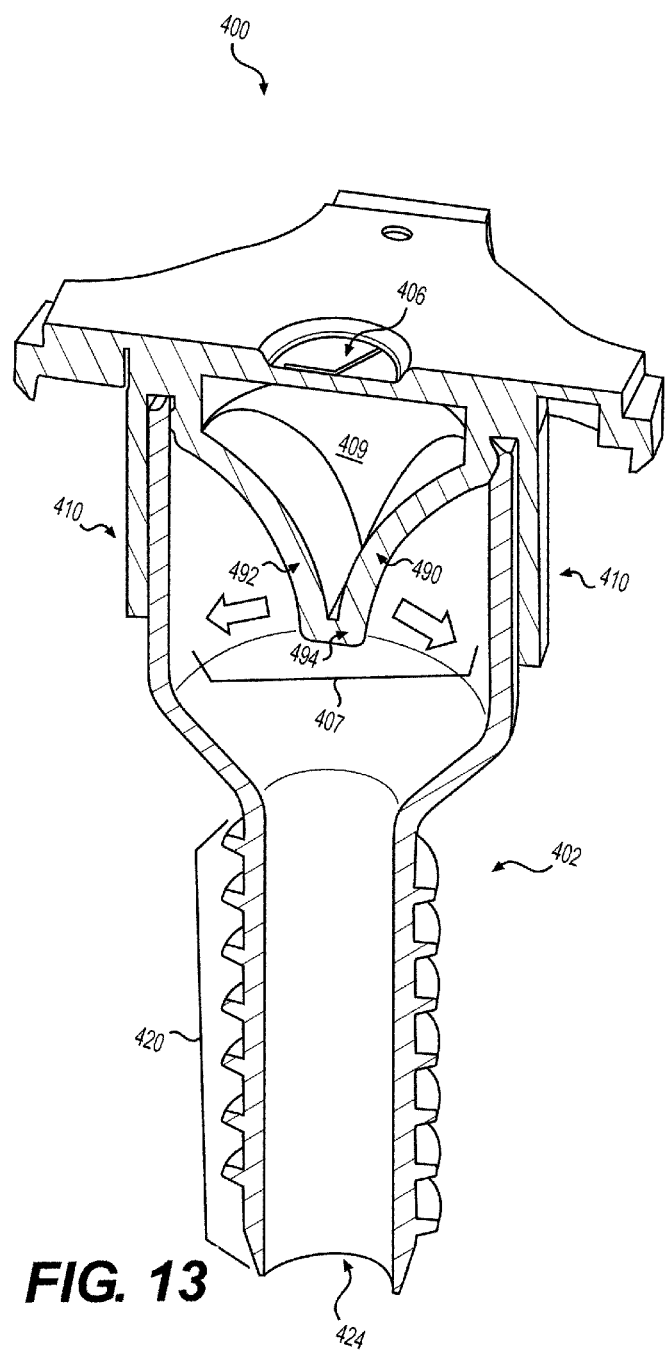
FIG. 13 is a second perspective cross-sectional view of the second embodiment of a surgical cannula in accordance with this disclosure.

Next, FIG. 13 shows a cross-sectional view with further structure of second valve 407. Namely, second valve 407 may be a duckbill valve that includes void 409 between second valve 407 and first valve 406. Second valve 407 may include first lip 490 and second lip 492 that come together at seam 494. When pressure is exerted on second valve 407 downward from the direction of first valve 406, first lip 490 and second lip 492 may part from each other as shown by the arrows in FIG. 13. However, in contrast, pressure exerted on second valve 407 upward from the direction of insertion portion 420 and distal opening 424 will not cause lips 490, 492 to part. Therefore, pressurized liquid will be retained within cannula body 402.

It will be noted that the embodiment shown in FIGS. 8-13 may also include a tether, such as shown and discussed with respect to the embodiment shown in FIGS. 1-7.

Figure 14:
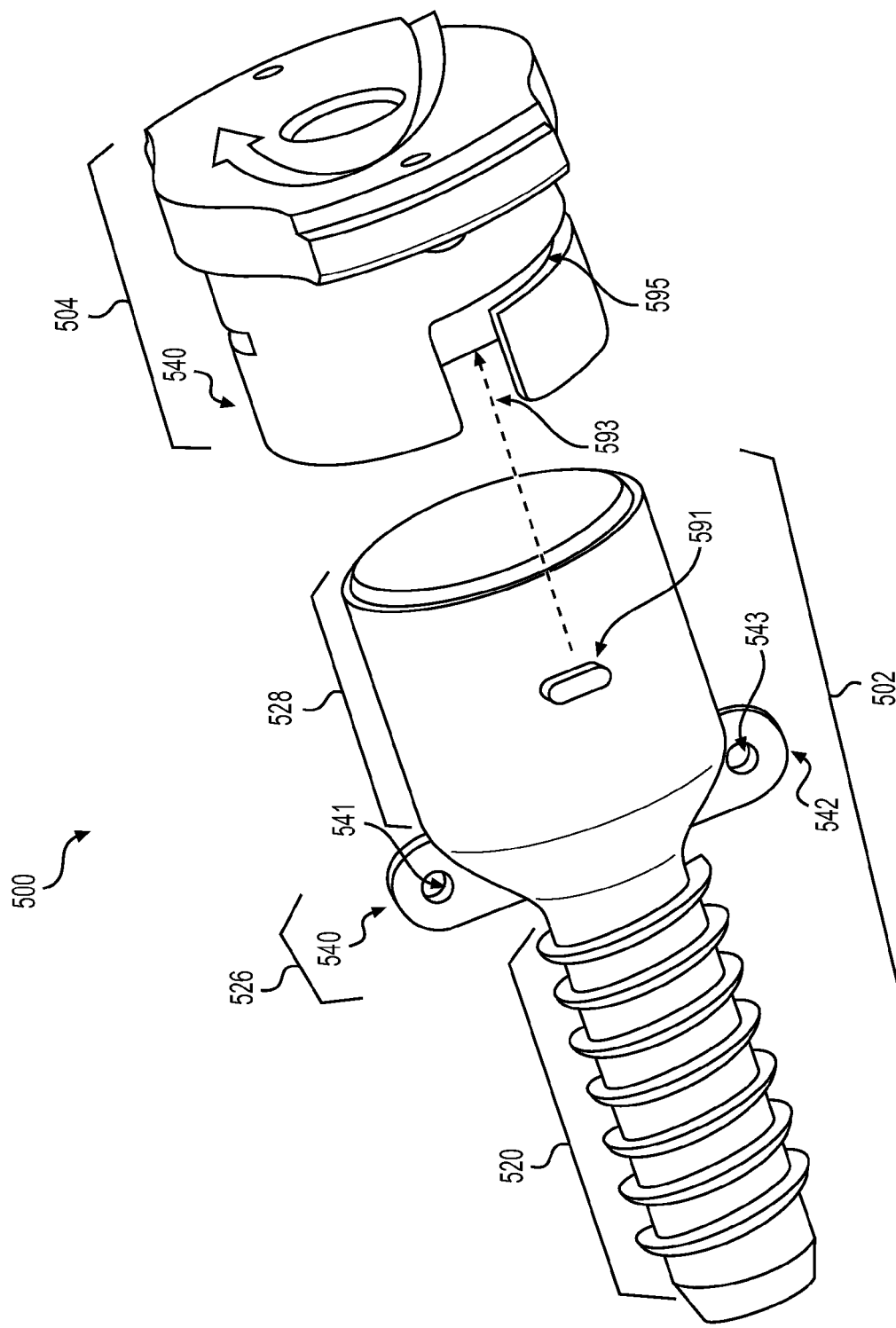
FIG. 14 is a perspective top view of a third embodiment of a surgical cannula in accordance with this disclosure.

FIG. 14 shows a third embodiment of a cannula 500 in accordance with this disclosure. Cannula 500 shares many features with cannula 400 as discussed above, but also differs with respect to several features. Namely, cannula 500 includes first suture attachment flange 540 including first eyelet 541 and second suture attachment flange 542 including second eyelet 543. First suture attachment flange 540 and second suture attachment flange 542 may be located on taper section 526 of cannula body 502, between insertion portion 520 and receiving portion 528. Flanges 540, 542 may extend laterally outward from cannula body 502. As discussed above with respect to first wing structure 440 and second wing structure 442, flanges 540, 542 may be used to anchor cannula 500 to tissue at an incision site by passing a thread of suture through one or more of eyelets 541, 542 and also through the skin proximate to the incision site.

Cannula 500 may also include retaining protrusion 591 on a side 510 of retaining portion 528. Retaining protrusion 591 may be used to retain seal structure 504 on cannula body 502. Namely, seal structure may include vertical cutout 593 and horizontal cutout 593. Retaining protrusion 591 may have a width that is the same as a width of vertical cutout 593, and retaining protrusion 591 may have a height that is the same as a height of horizontal cutout 595. In this way, retaining protrusion 591 may be moved along vertical cutout 593 when cannula body 502 and seal structure 504 are brought together. Then, retaining protrusion 591 may be moved along horizontal cutout 595 by rotating seal structure 504 as shown by the arrow in FIG. 14. In this way, retaining protrusion 591 may keep seal assembly 504 removably engaged with the receiving portion 528 of cannula body 502.

Figure 15:
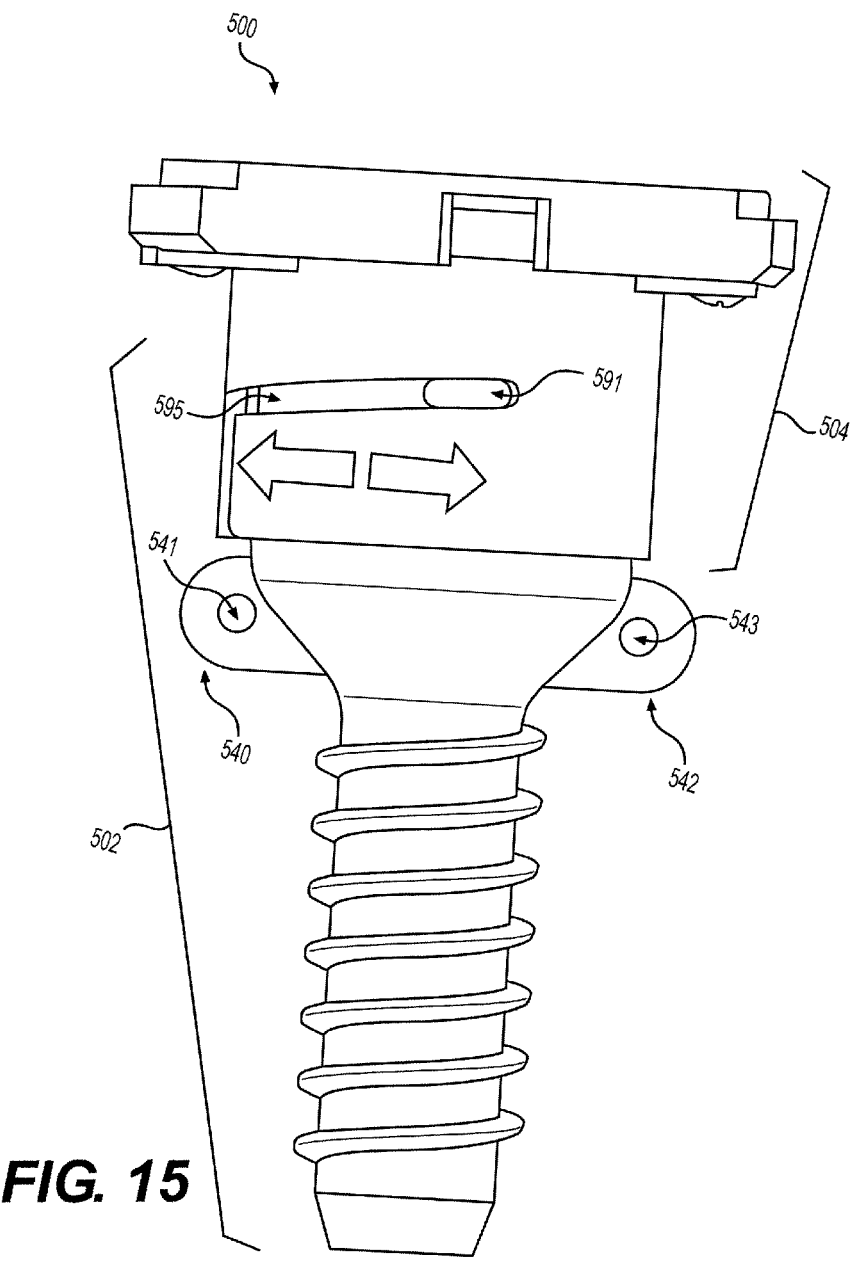
FIG. 15 is a side view of the third embodiment of a surgical cannula in accordance with this disclosure.

FIG. 15 further shows features of cannula 500. Namely, in FIG. 15, seal structure 504 is engaged with cannula body 502 by the disposition of retaining protrusion 591 within horizontal cutout 595. Seal structure 504 may be rotated clockwise or counterclockwise in order to move retaining protrusion 591 within horizontal cutout 595, so as to disengage seal structure 504 from cannula body 502.

Figure 16:
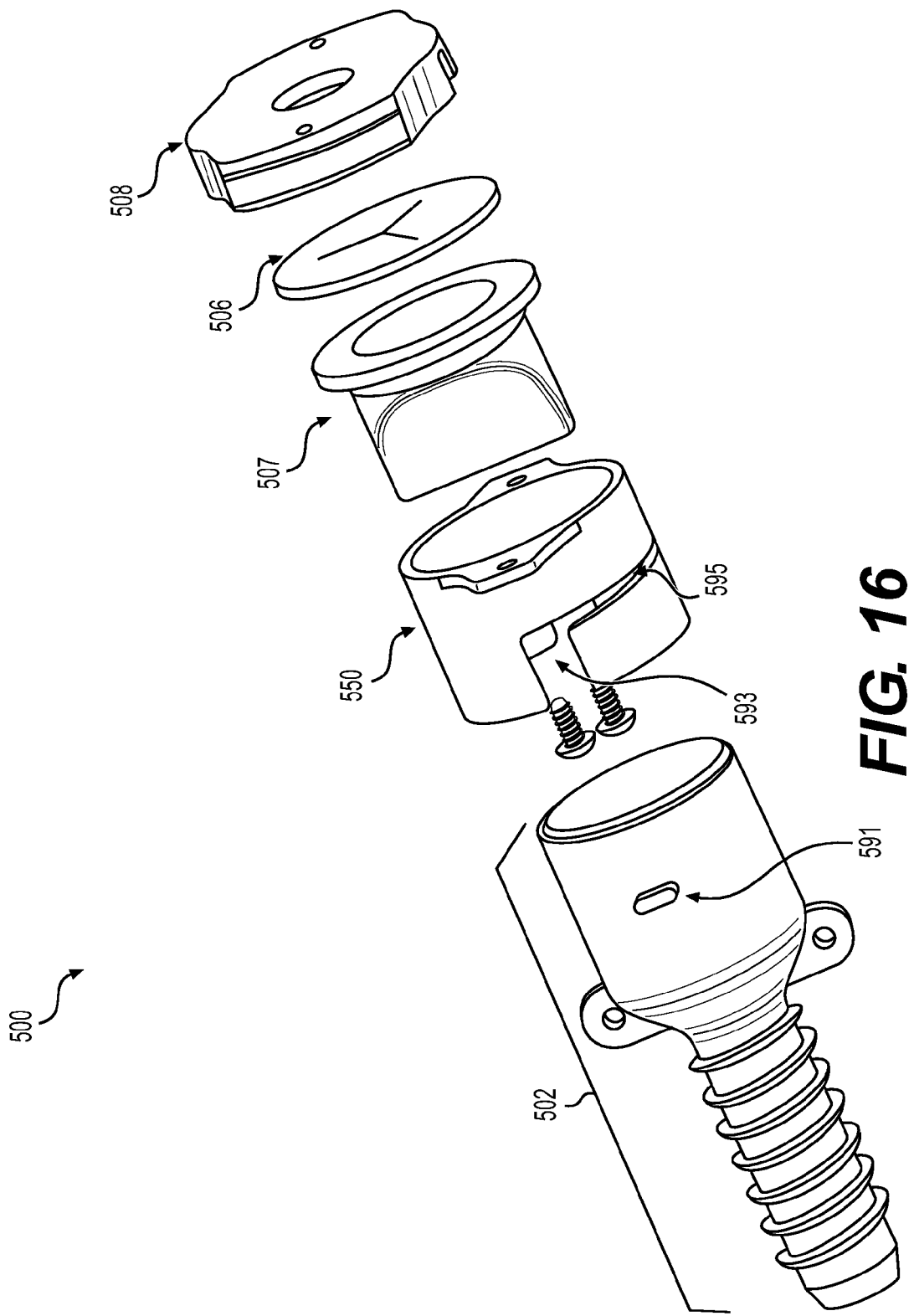
FIG. 16 is a first side exploded view of the several subcomponents of the third embodiment of a surgical cannula in accordance with this disclosure.

FIG. 16 shows an exploded view of the several subcomponents that may make up cannula 500. Namely, cannula 500 may include: cannula body 502 that may include retaining protrusion 591, lower housing portion 550 that may include vertical cutout 593 and horizontal cutout 595, first valve 506 which may be a tricuspid valve, second valve 507 which may be a duckbill valve, and housing cover 508.

Figure 17:
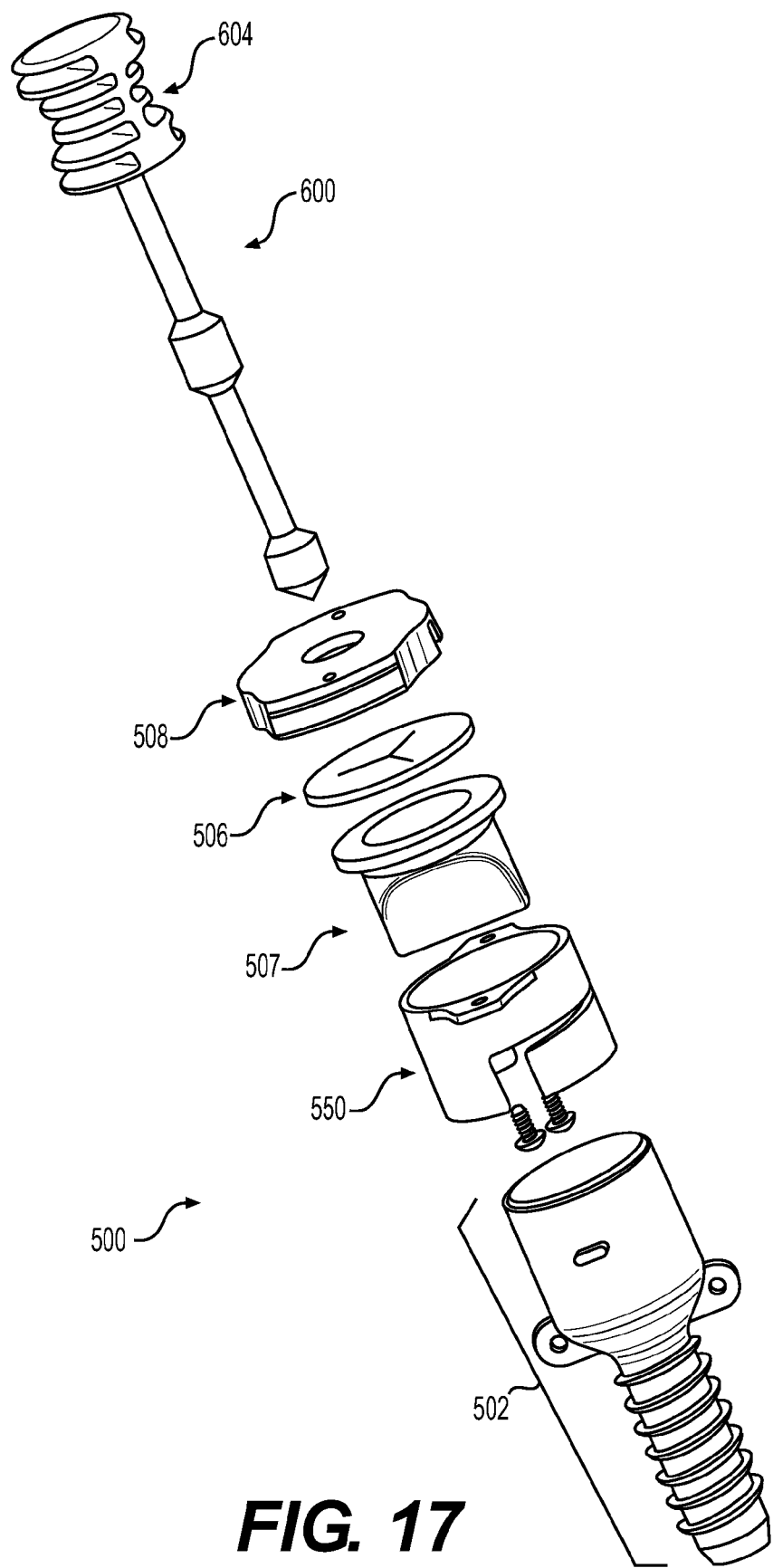
FIG. 17 is a second side exploded view of the several subcomponents of the third embodiment of a surgical cannula in accordance with this disclosure, and a tool used in conjunction with the cannula.

FIG. 17 shows an exploded view of the several subcomponents that may make up cannula 500, and also a tool 600. Tool 600 may be used during a surgical procedure, such as shown in FIG. 4, in conjunction with cannula 500. Namely, tool 600 may extend through first valve 506 and second valve 507 so as to reach a surgical site inside a body. First valve 506 and second valve 507 may retain a pressure seal against tool 600, such that pressurized surgical irrigation fluid may be retained within the surgical site while tool 600 is being used. Tool 600 is illustrated as an obturator. However, it will be noted that any of various types of elongate tools may be utilized with the disclosed cannulas. For example, probes, grasps, and other tools including long shafts against which the disclosed valves may seal may be utilized with the disclosed cannulas.

Next, FIG. 18 shows a cross-sectional view of cannula 500. This view shows how cannula 500 may include first retaining protrusion 591 and also second retaining protrusion 597. First retaining protrusion 591 may align with first vertical cutout 593 and first horizontal cutout 595 as discussed, while second retaining protrusion 597 may align with second vertical cutout 599 and second horizontal cutout (not shown in FIG. 18).

First retaining protrusion 591 and second retaining protrusion 597 may be located on opposite sides of cannula body 502 from each other. In this way, the two retaining protrusions 591, 597 may ensure a snug and tight fit between cannula body 502 and seal structure 504 that retains pressurized surgical liquid.

It will be noted that the embodiment shown in FIGS. 14-18 may also include a tether, such as shown and discussed with respect to the embodiment shown in FIGS. 1-7.

A fourth embodiment of a surgical cannula in accordance with this disclosure is shown in FIGS. 19-22. Namely, as shown in at least FIG. 19, surgical cannula 700 may include a cannula body 702 and a seal structure 704. Cannula body 702 may be substantially similar to cannula body 102, cannula body 402, and cannula body 502 as discussed above, in some respects. However, in other aspects, cannula body 702 may differ from other embodiments disclosed herein, as discussed below.

In particular, cannula body 702 may include insertion portion 720, receiving portion 728, and taper portion 726 between insertion portion 720 and receiving portion 728. Insertion portion 720 may be configured to be inserted into tissue, such as a human body or an animal body, and may be generally cylindrical in shape. Insertion portion 720 may also include threads 722 on an exterior surface thereof. Taper portion 726 may be configured to roll up a graft upon insertion through the cannula, as described above.

Cannula body 702 may also include first suture attachment flange 740 including first eyelet 741 and second suture attachment flange 742 including second eyelet 743. First suture attachment flange 740 and second suture attachment flange 742 may be located on taper section 726 of cannula body 702, between insertion portion 720 and receiving portion 728, on laterally opposite sides of cannula body 702 from each other. Flanges 740, 742 may extend laterally outward from cannula body 702. As discussed above, flanges 740, 742 may be used to anchor cannula 700 to tissue at an incision site by passing a thread of suture through one or more of eyelets 741, 742 and also through the skin of the patient proximate the cannula insertion site.

Figure 19:
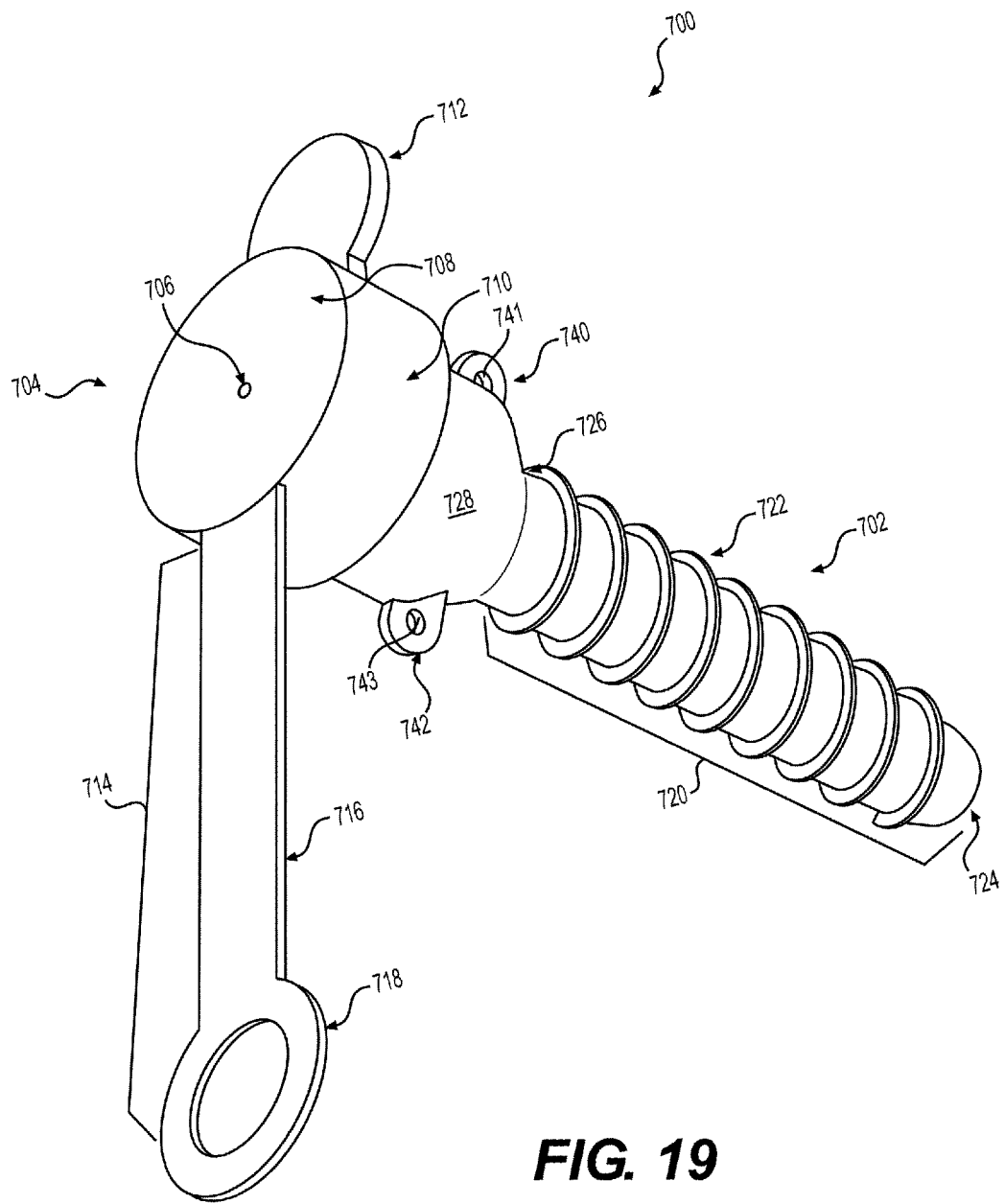
FIG. 19 is a perspective top view of a fourth embodiment of a surgical cannula in accordance with this disclosure.

FIG. 19 also shows various details of seal structure 704. In particular, seal structure 704 may include a through-hole 706 on a top surface 708. Through-hole 706 may have a first diameter that is sufficiently large as to allow a tool such as obturator tool 600 (shown in FIG. 17) to pass through and enter into the cannula 700. For example, in some embodiments, seal structure 704 may be made from an elastomeric material—such that through-hole 706 first diameter may be smaller than the diameter of a tool 600 and yet also stretch to expand to allow tool 600 into the cannula 700. In this embodiment, top surface 708 may press against tool 600 when it is inserted into through-hole 706 so as to form a seal around tool 600. This may advantageously allow seal structure 704 to retain pressure within cannula 700 during use.

Seal structure 704 may also include tab portion 712. Tab portion 712 may be connected to side portion 710 of seal structure 704. Tab portion 712 may allow a user to easily and conveniently remove seal structure 704 from engagement with cannula body portion 702 by grasping onto tab portion 712.

Seal structure 704 may also include tether 714. Tether 714 may connect seal structure 704 to cannula body portion 702 when seal structure 704 is not engaged with receiving portion 728. Namely, when a user such as a surgeon removes seal structure 704 from cannula body portion 702 during use, tether 714 may ensure that seal structure 704 is not lost or otherwise distantly separated. Tether 714 may include ring 718 and arm 716. Tether ring 718 may be configured to surround insertion portion 720 of cannula body 702. Tether arm 716 may have sufficient length to allow seal structure 704 to be removed from cannula body 702 and located out of the way of a surgical procedure, when needed.

Figure 20:
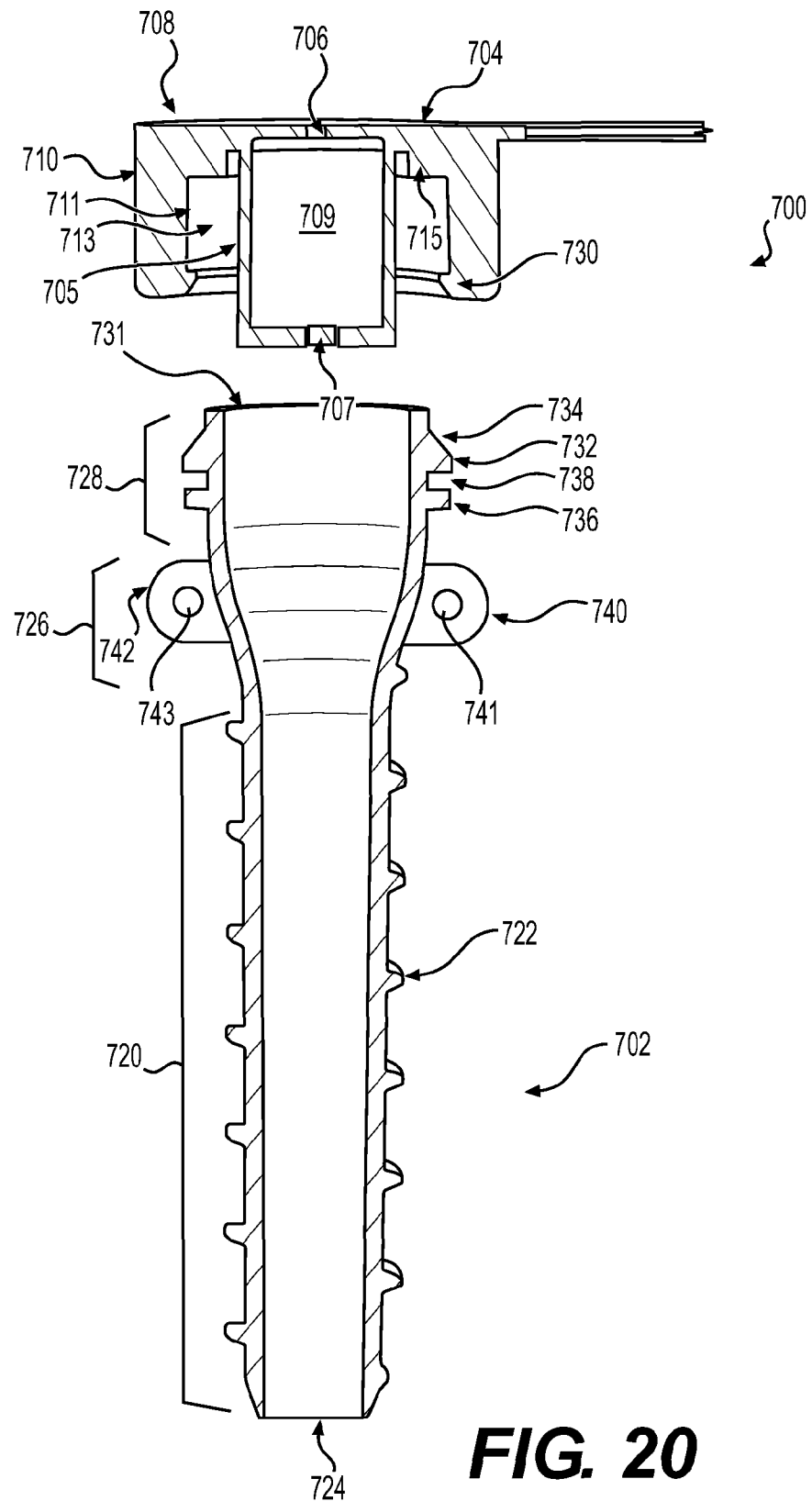
FIG. 20 is a cross-sectional view of the fourth embodiment of a surgical cannula in accordance with this disclosure.

FIG. 20 shows a cross-sectional view of the fourth embodiment of a surgical cannula 700. This view shows how cannula body portion 702 may include threads 722 that wrap around insertion portion 720, how first suture attachment flange 740 and second suture attachment flange 742 may be disposed on opposite sides of taper portion 726 from each other, and how receiving portion 728 may include several structures configured to engage with seal structure 704.

In particular, receiving portion 728 of cannula body 702 may include a first retaining lip 732. First retaining lip 732 may be located adjacent to proximal opening 723 of cannula body 702. First retaining lip 732 may also include a sloped top surface 734. Sloped top surface 734 may therefore result in first retaining lip 732 gradually increasing in width, as measured outward laterally from cannula body portion 702. Receiving portion 728 may also include a second retaining lip 736 that also extends outward laterally from receiving portion 728 of cannula body portion 702. Second retaining lip may be located closer to distal opening 724 than first retaining lip 732. First retaining lip 732 and second retaining lip 736 may be located a small distance apart from each other, so as to form a retaining groove 738 between them.

This configuration of first retaining lip 732, retaining groove 738, and second retaining lip 736 may allow seal structure 704 to reversibly engage with cannula body portion 702 in such a way as to retain pressure within the surgical cannula 700 when in use. Specifically, seal structure 704 may include a retaining hook structure 730 that extends laterally inward from a sidewall 710 of the seal structure 704. In particular, retaining hook structure 730 may extend laterally inward from an inner surface 711 of sidewall 710. In this way, retaining hook structure 730 may slide past first retaining lip 732, and become lodged in retaining groove 738 between first retaining lip 732 and second retaining lip 736 when engaged. In some embodiments, seal structure 704 may be comprised of an elastomeric material that bends or stretches within some range—and in such embodiments, sidewall 710 may flex laterally outward so as to allow retaining hook structure 730 to slide along top surface 734 of first retaining lip 732 so as to become reversibly engaged in retaining groove 738. In some embodiments, seal structure 704 may be configured such that retaining hook structure 730 extends below second retaining lip 736. In such configurations, having the two retaining lips may provide two separate seals with the inner surface 711 of seal structure 704.

FIG. 20 also shows how, in this embodiment, seal structure 704 may further include a tricuspid valve 707. Tricuspid valve 707 may be located in line with through-hole 706, so that a tool 600 may be inserted through both tricuspid valve 707 and through-hole 706 when cannula 700 is being used in a surgical procedure. Specifically, seal structure 704 may include a cavity 709 that is created by top surface 708, cavity sidewall 705, and bottom surface 717. Cavity 709 may be configured to retain pressure therein, and catch any seepage of a pressurized fluid that may come through tricuspid valve 707 when the cannula 700 is in use.

In some embodiments, tricuspid valve 707 may have a second diameter that is larger than first diameter of through-hole 706. Tricuspid valve 707 may therefore allow a tool 600 to maneuver with some degree of lateral movement while inserted through surgical cannula 700, as shown in FIG. 4 and discussed above. In this way, smaller first diameter of through-hole 706 may ensure an at least partial seal against tool 600 while valve 707 (having larger second diameter) may create a second seal against the tool while still allowing the tool necessary movement. As a result, through-hole 706 and valve 707 may collectively ensure that pressure is retained within cannula 700 when in use.

Figure 21:
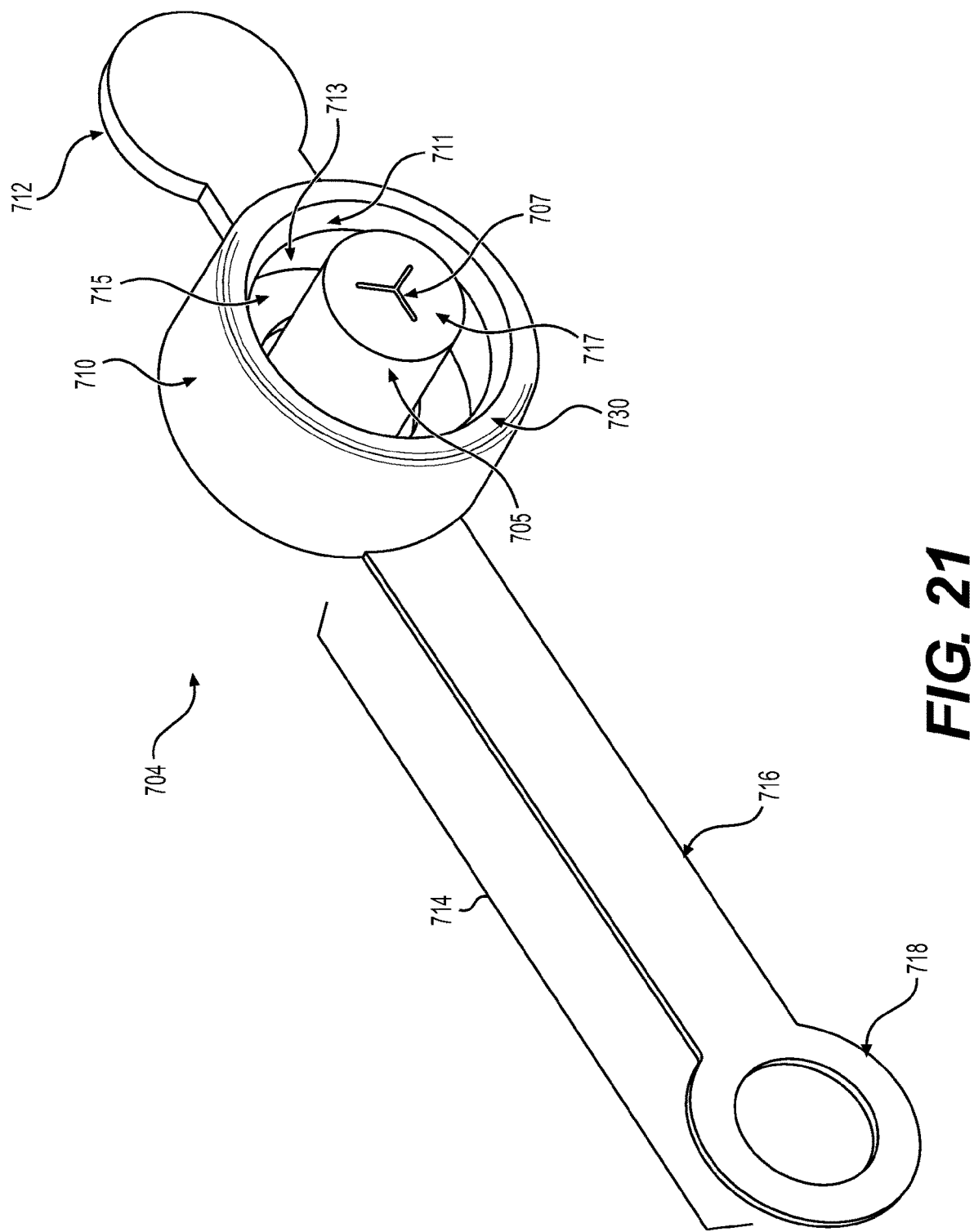
FIG. 21 is a perspective bottom view of the fourth embodiment of a surgical cannula in accordance with this disclosure.

Next, FIG. 21 shows a perspective bottom view of seal structure 704. Specifically, FIG. 21 shows additional details of the underside of the seal structure 704 and the related structures that allow seal structure 704 to reversibly engage with cannula body portion 702 (FIG. 20). Namely, as shown in FIG. 21, seal structure 704 may include tricuspid valve 707 on bottom surface 717. Tricuspid valve 707 may therefore extend downward into receiving portion 728, such that cavity sidewall 705 may be adjacent to an inner surface of receiving portion 728 (as shown in FIG. 20). Receiving portion 728 may therefore be contained within opening 713, that is created between inner surface 711 of sidewall 710 and cavity sidewall 705.

In some embodiments, as shown in FIG. 21, the seal structure 704 may be formed of a continuous unitary piece material. In some particular embodiments, seal structure 704 may be a unibody continuous piece of an elastomeric material.

Also shown in FIG. 21 is retaining hook structure 730—and how retaining hook structure 730 extends circumferentially around a bottom perimeter of sidewall 710. In such embodiments, retaining hook structure 730 may therefore form a continuous seal around the entirety of receiving portion 728 of cannula body portion 702. This may advantageously allow seal structure 704 to retain pressure therein when in use in a surgical procedure.

Figure 22:
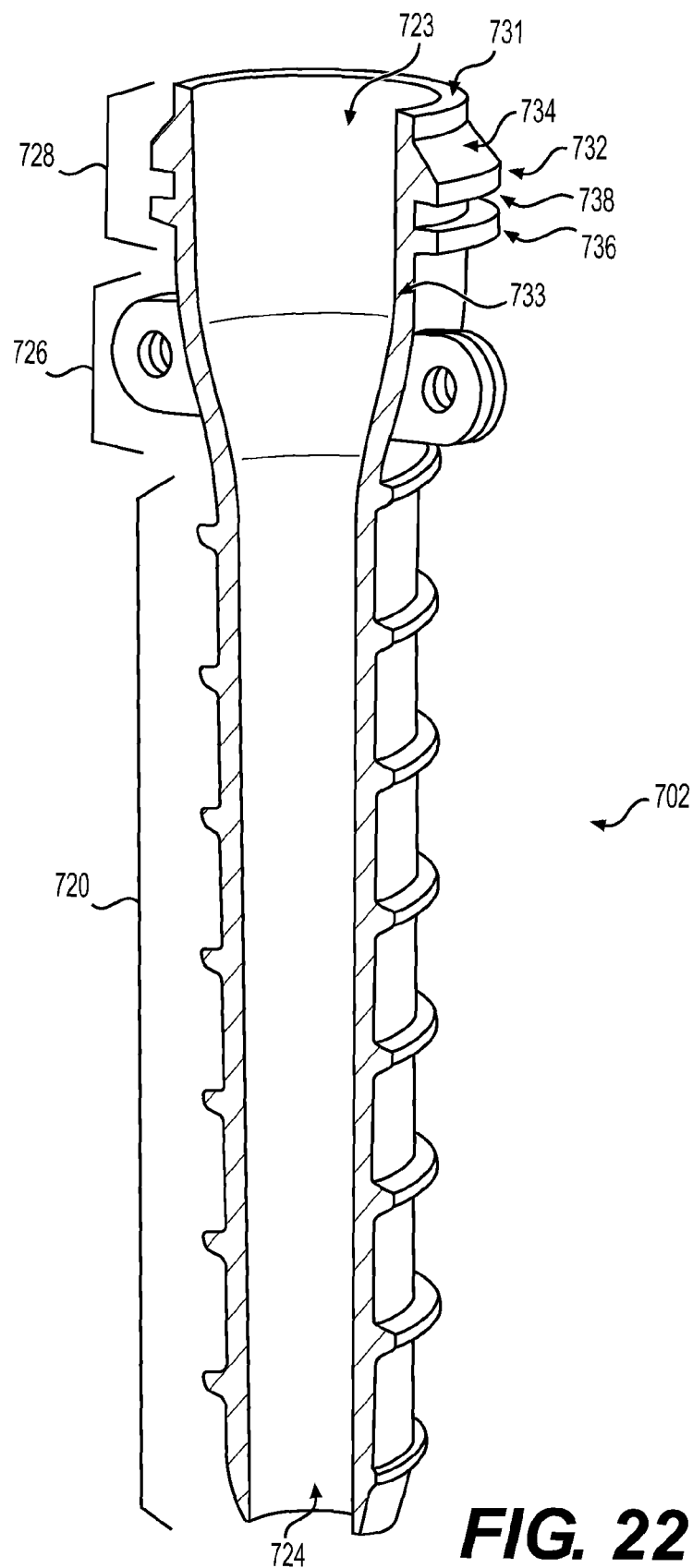
FIG. 22 is an perspective cross-sectional view of the fourth embodiment of a surgical cannula in accordance with this disclosure.

FIG. 22 shows a perspective cross-sectional view of cannula body portion 702. In this view, additional details of first retaining lip 732 and second retaining lip 736 are shown. Specifically, first retaining lip 732 extends circumferentially around receiving portion 728. Second retaining lip 736 may also similarly extend circumferentially around receiving portion 728. In this way, retaining groove 738 may extend around the entire circumference of cannula body portion 702 so as to allow retaining hook structure 730 to set therein. Again, as described above, in some embodiments, retaining hook structure 730 may be disposed distally of second retaining lip 736 when the seal structure is engaged with cannula body portion 702.

Additionally, FIG. 22 shows cannula receiving portion 728 top surface 731. Top surface 731 may, in accordance with FIG. 20, rest against inner surface 715 (see FIG. 21) of seal structure 704 so as to further ensure a proper seal is created between cannula body portion 702 and seal structure 704.

Figure 23:
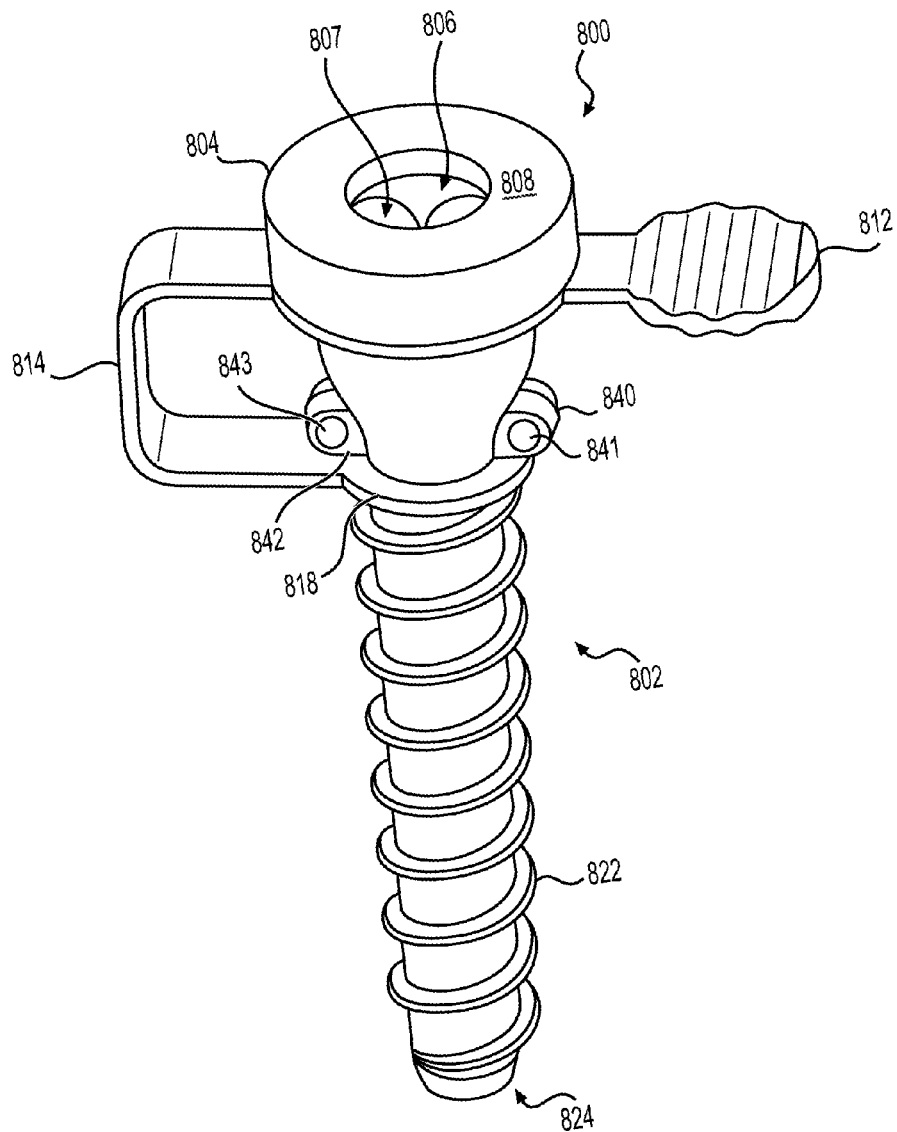
FIG. 23 is a perspective view of a fifth embodiment of a surgical cannula in accordance with this disclosure.

Next, a fifth embodiment of a surgical cannula is shown in FIGS. 23-29. FIG. 23 shows a perspective view of a surgical cannula 800. Surgical cannula 800 may include various features having similarities with the other embodiments of surgical cannulas discussed herein.

Specifically, surgical cannula 800 may include a cannula body 802 and a seal structure 804. Seal structure 804 may include tether 814, that includes tether ring 818, and tab portion 812. In this embodiment, seal structure 804 may include through-hole 806 on top surface 808. Through-hole 806 may have a larger diameter than e.g. through-hole 706 in order to accommodate different types of surgical tools. In some embodiments, diameter of through-hole 806 may be at least 50% of a diameter of top surface 808. Within through-hole 806, valve 807 is contained inside seal structure 804.

Cannula body 802 may include threads 822 on an outer surface thereof, as shown. Cannula body 802 may also include distal opening 824 disposed opposite through-hole 806. Additionally, cannula body 802 may include first suture attachment flange 840 (with first eyelet 841 therein) and second suture attachment flange 842 (with second eyelet 843 therein).

Figure 24:
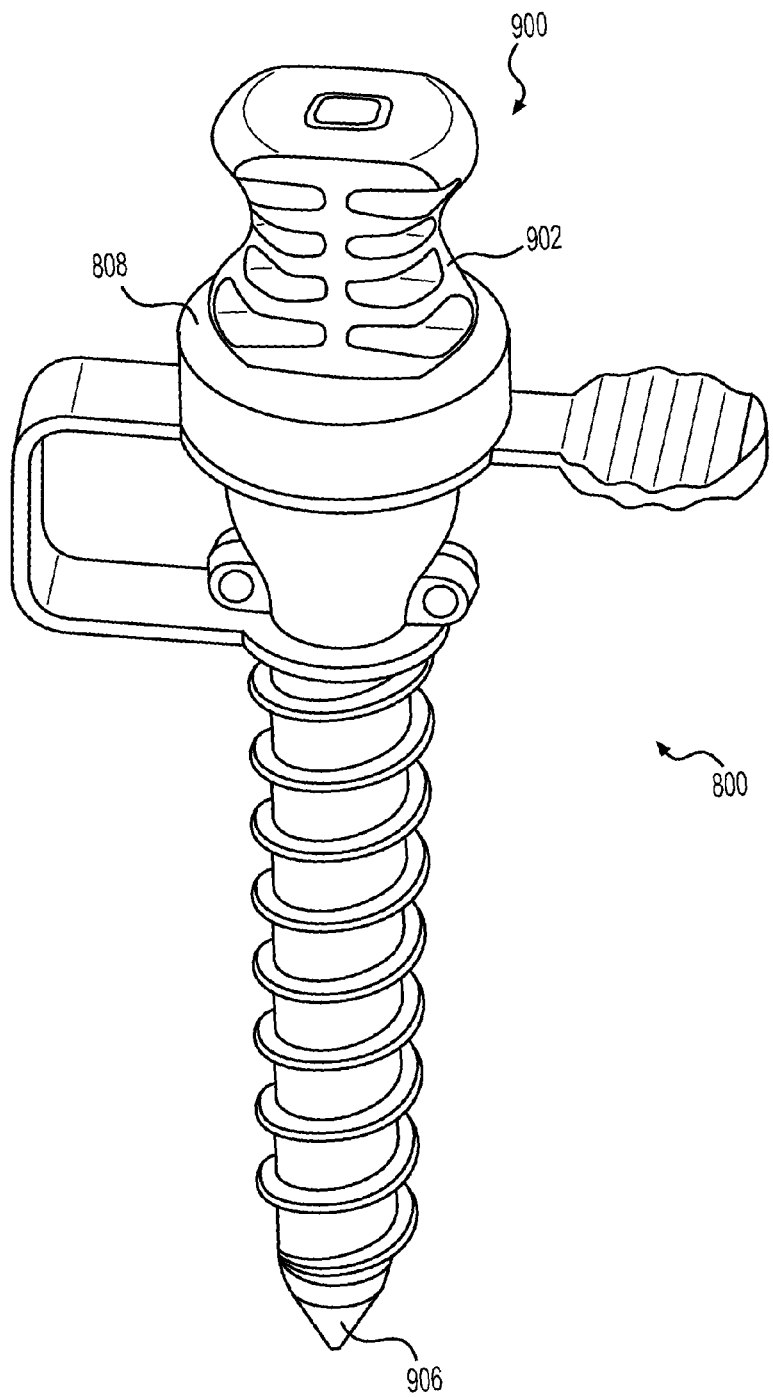
FIG. 24 is a perspective view of the fifth embodiment of a surgical cannula with a tool therein.

FIG. 24 is a perspective view of the fifth embodiment of a surgical cannula 800 with a tool 900 therein. As shown in FIG. 24, tool 900 may be an obturator. However, it will be understood that any various types of elongated instruments may be inserted through cannula 800. Tool 900 may be inserted into through-hole 806, extend along cannula body 802, and a portion 906 of tool 900 may extend out of distal opening 824. Tool handle 902 may abut top surface 808 of seal structure 804 on surgical cannula 800. In this way, tool 900 may be used during a surgical procedure by being inserted into surgical cannula 800. For example, cannula 800 may be inserted through tissue using tool (obturator) 900 to facilitate the piercing of the tissue.

Figure 25:
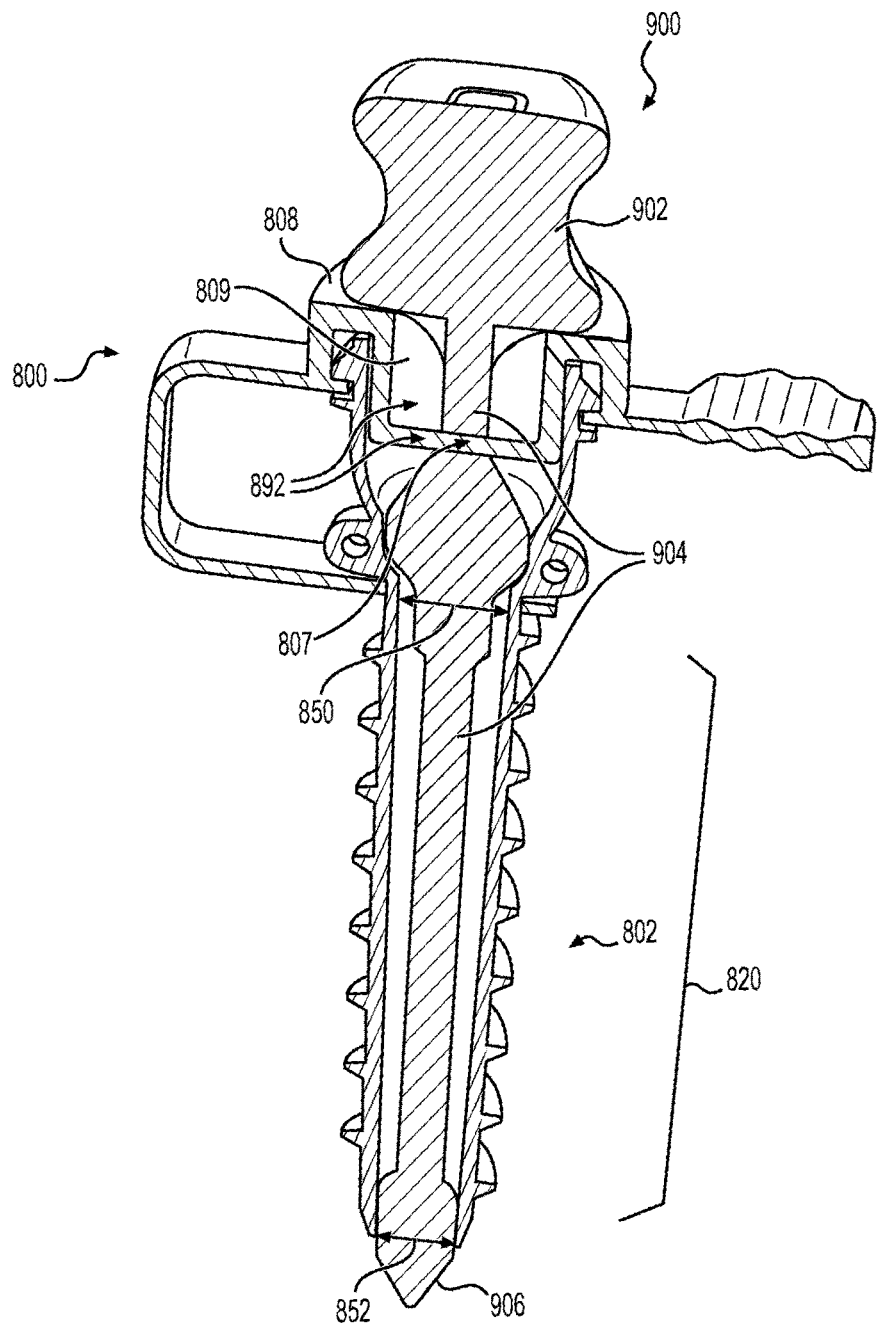
FIG. 25 is a perspective cross-sectional view of the fifth embodiment of a surgical cannula with the tool therein.

FIG. 25 is a perspective cross-sectional view of tool 900 as inserted into surgical cannula 800. Namely, tool 900 shaft 904 may extend in through-hole 806, and through valve 807 such that valve 807 forms a seal around tool shaft 904. In this way, valve 807 may separate fluid contained within cannula body 802 during a surgical procedure from an outer area 809 exposed to outside air. Additionally, FIG. 25 also shows how in some embodiments the width of cannula body may vary along insertion portion 820. Namely, insertion portion 820 may have first width 850 at one end of insertion portion 820 and second width 852 at distal opening 852 that is the opposite end of insertion portion 820. First width 850 may be greater than second width 852.

Figure 26:
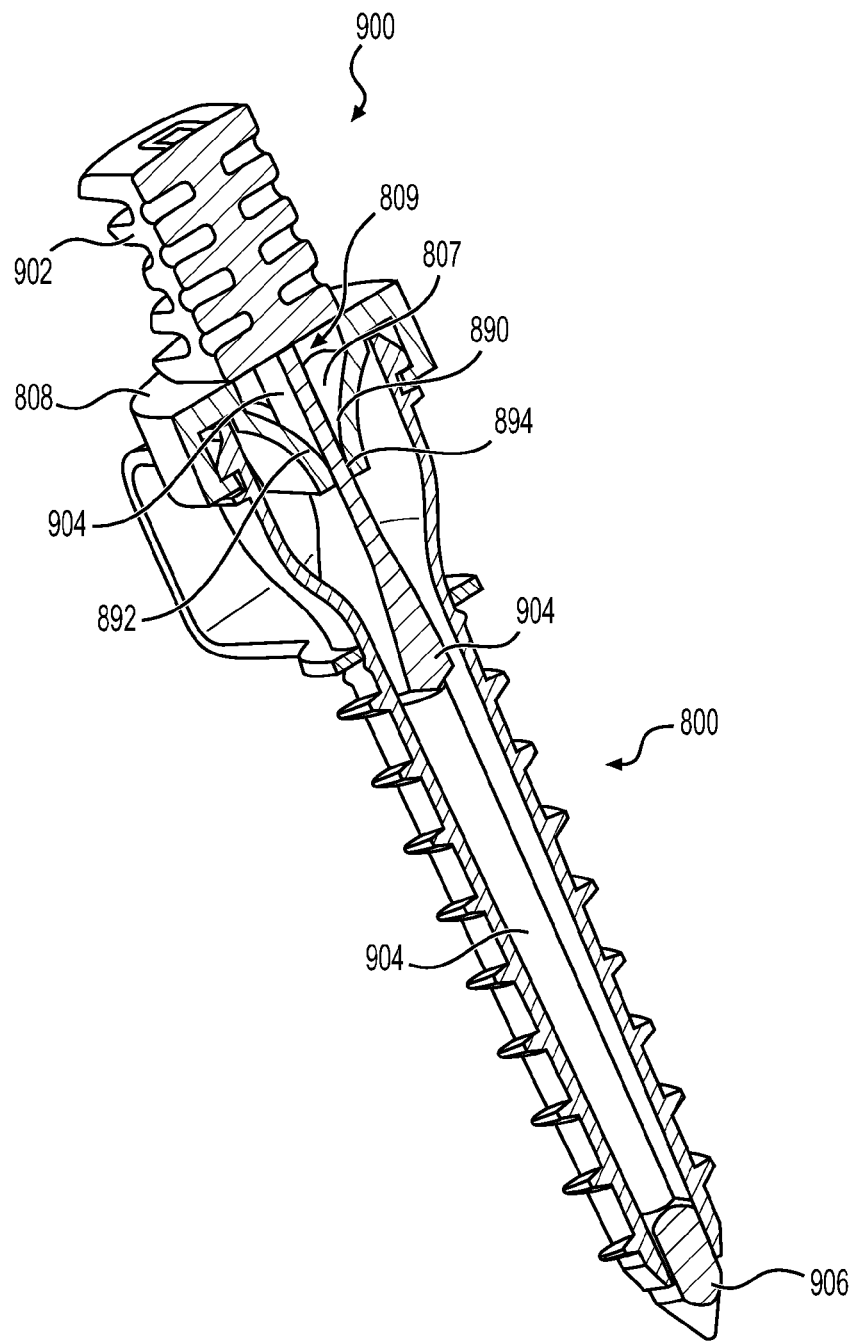
FIG. 26 is a second perspective cross-sectional view of the fifth embodiment of a surgical cannula with the tool therein.

FIG. 26 shows in particular how valve 807 may form a seal around tool 900 shaft 904. In this embodiment, valve 807 may be a duckbill valve—and may be similar to duckbill valve 507 discussed above with respect to surgical cannula 500. Specifically, valve 507 may include first lip 890 and second lip 892 that come together at seam 894. In this way, the two lips 890, 892 may form a seal around tool 900 as shaft 904 extends through seam 894 and down through the remainder of cannula body 802 until portion 906 extends out distal opening 824.

Figure 27:
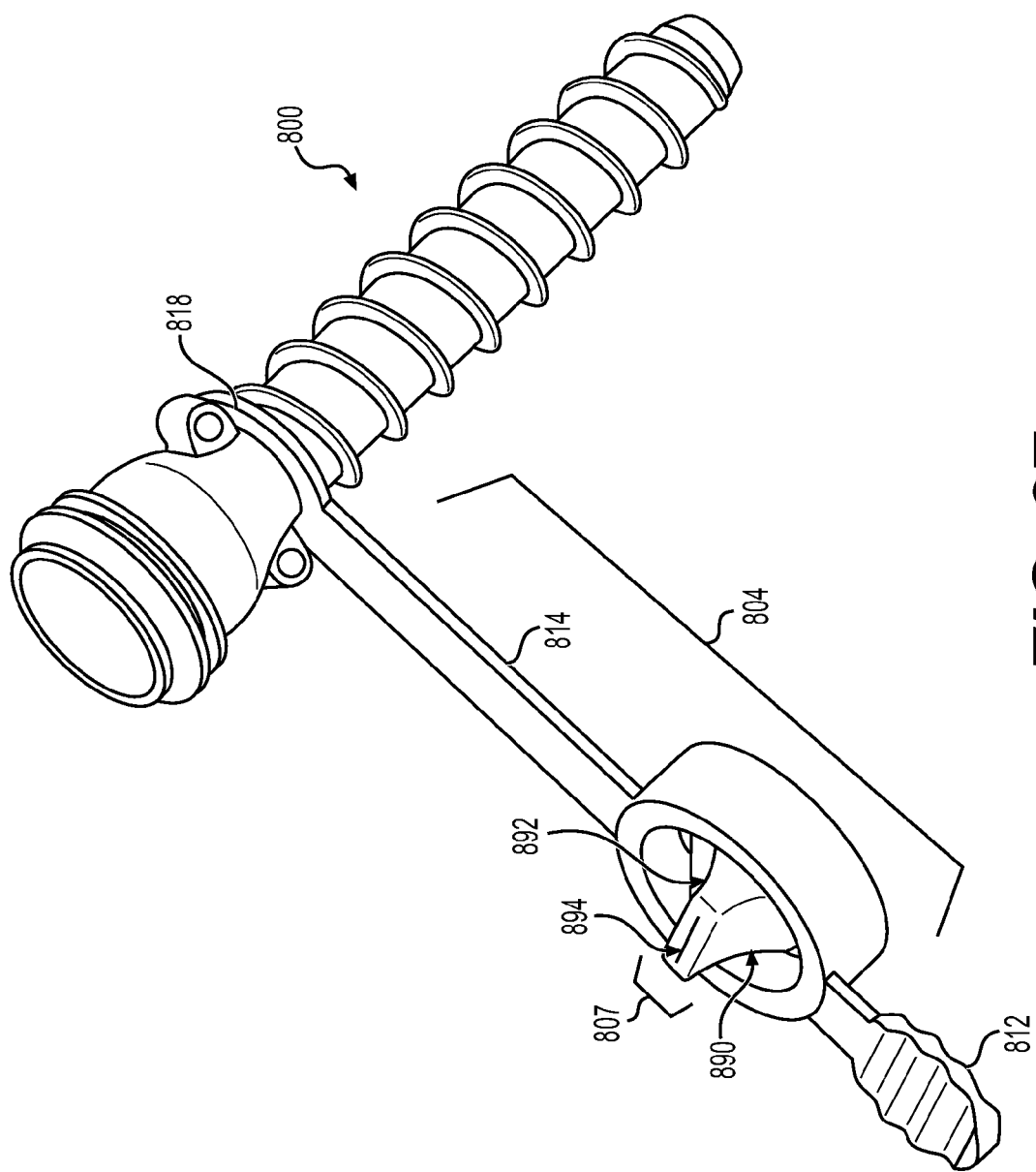
FIG. 27 is a perspective view of the fifth embodiment of a surgical cannula with the seal structure removed from the receiving portion of the cannula body.

FIG. 27 is a perspective view of surgical cannula 800 with seal structure 804 removed from cannula body 802. In this underside view of seal structure 804, the structure of valve 807 may be seen in greater detail. That is, valve 807 includes first lip 890 and second lip 892 that meet at seam 894. When no tool 900 is inserted into cannula 800, valve 807 in its resting position, as shown in FIG. 27, forms a seal that prevents liquid or air to pass through when seal structure 804 is installed onto cannula 800.

Figure 28:
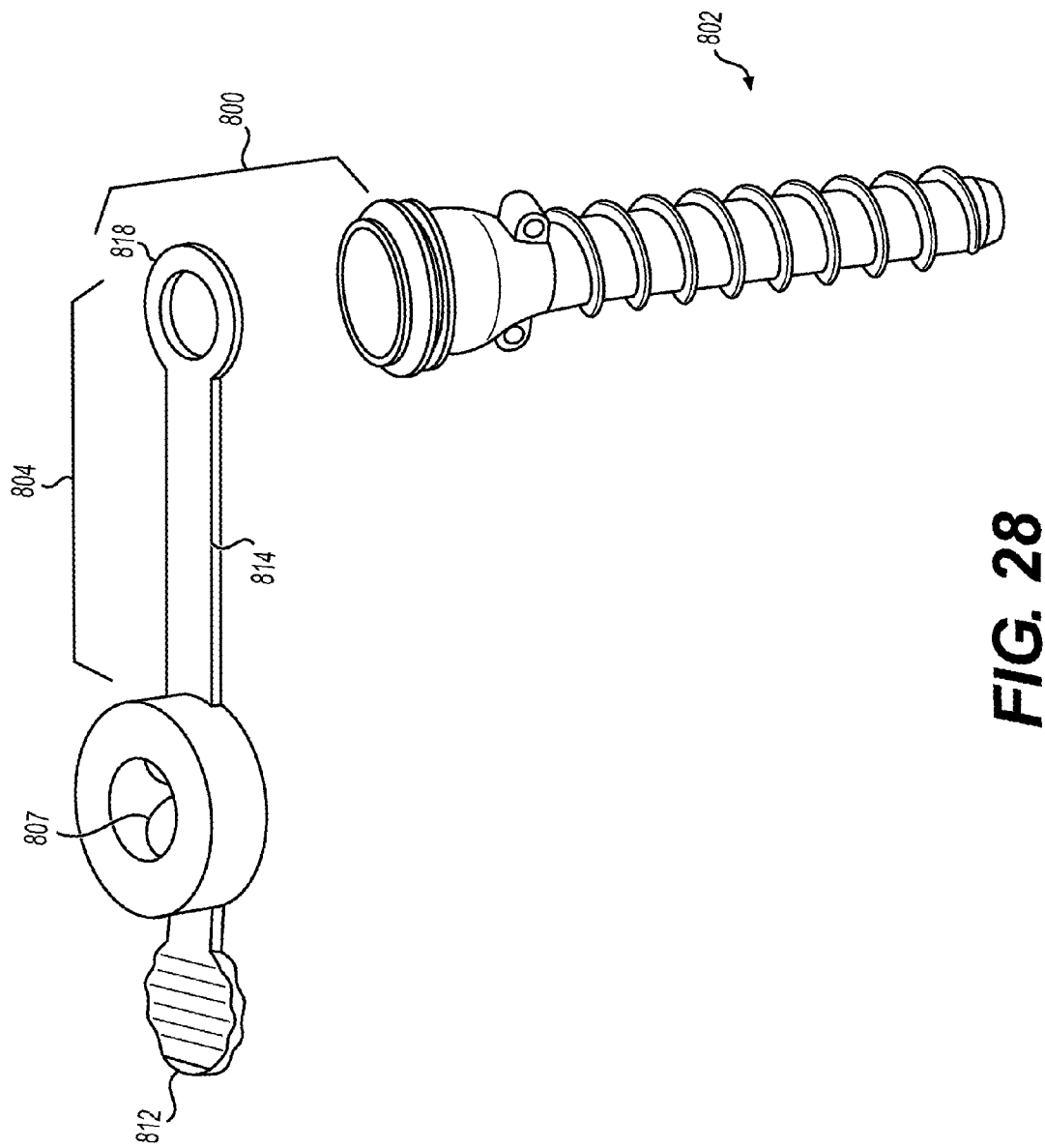
FIG. 28 is a top perspective view of the fifth embodiment of a surgical cannula with the seal structure and tether entirely removed from the cannula body.

FIG. 28 is a top perspective view of surgical cannula 800 with seal structure 804 entirely removed from cannula body 802. As discussed above with respect to other embodiments, seal structure 804 may include tether 814 and tether ring 818 that are configured to secure seal structure 804 to cannula body 802. In this way, a medical practitioner may use tab portion 812 to reversibly remove seal structure 804 from cannula body 802 without losing track of seal structure 804, as may be necessary during a surgical procedure.

Figure 29:
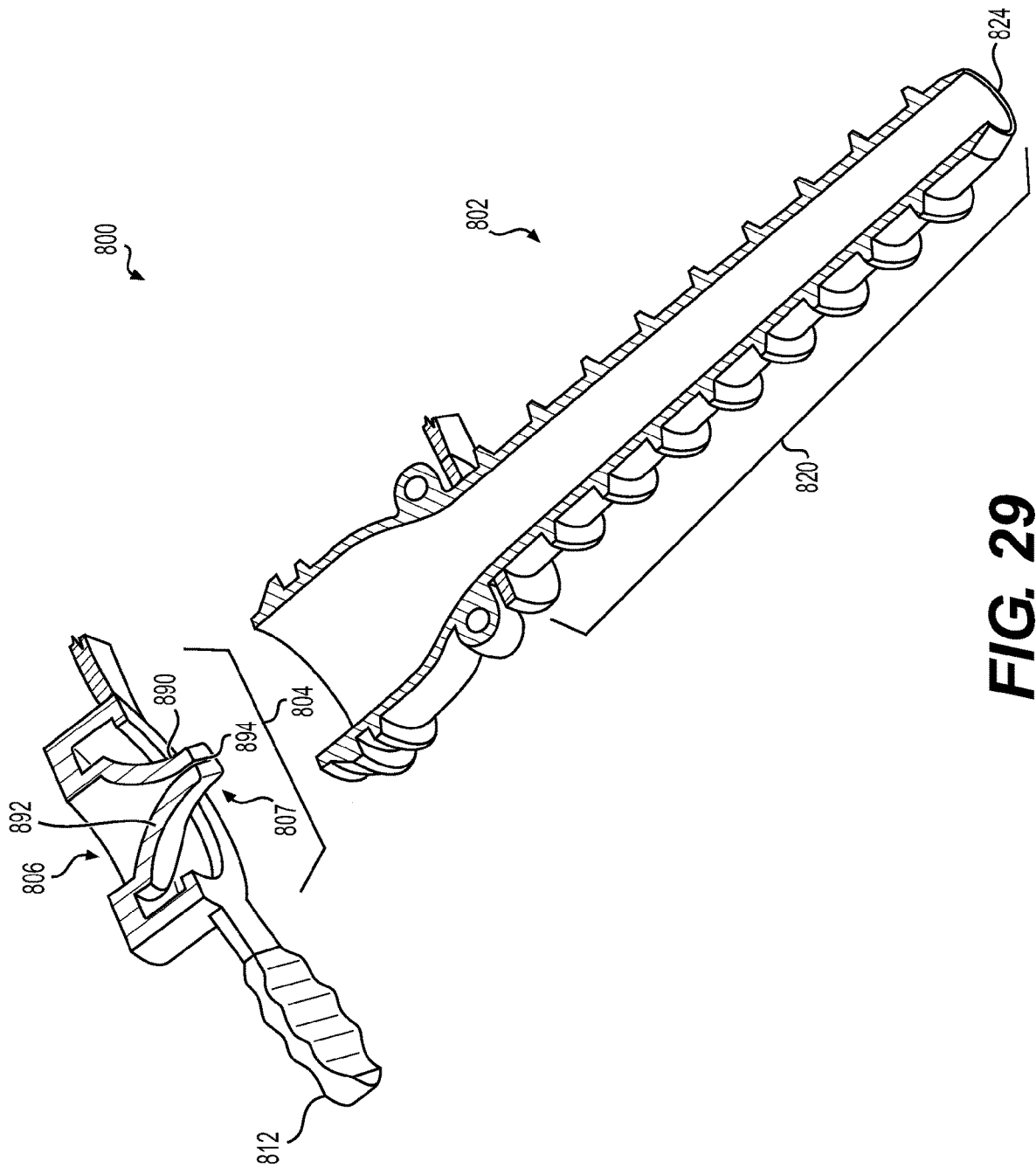
FIG. 29 is a cross-sectional perspective view of the fifth embodiment of a surgical cannula with the seal structure removed from the cannula body.

Finally, FIG. 29 is a cross-sectional perspective view of surgical cannula 800 with seal structure 804 removed from cannula body 802. In this view, valve 807 is again clearly depicted as a duckbill valve having two lips 890, 892 that meet at seam 894. This figure also shows how seal structure 804 may be reversibly attached to cannula body using retaining lip structures that may be substantially the same as discussed above with respect to surgical cannula 700.

With respect to any embodiment discussed above, a cannula body portion in accordance with this disclosure may be substantially rigid. In some embodiments, the cannula body portion may be formed, at least in part, from a rigid material selected from the group consisting of polycarbonate and polypropylene.

While various embodiments are described, the description is intended to be exemplary, rather than limiting and it will be apparent to those of ordinary skill in the art that many more embodiments and implementations are possible that are within the scope of the disclosed embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted. Further, unless otherwise specified, any step in a method or function of a system may take place in any relative order in relation to any other step described herein.

We claim:

1. A surgical cannula, comprising:
   a seal structure including at least a first valve, the first valve being a one-way check valve configured to open in response to pressure applied onto the first valve from one direction but not from an opposite direction; and
   a continuous unitary piece of material forming a cannula body, including:
   an insertion portion having a distal opening that is configured to be inserted into tissue, and
   a receiving portion that includes a proximal opening and is configured to reversibly receive the seal structure;
   the cannula body defining a longitudinal axis extending from the proximal opening to the distal opening;
   wherein the seal structure is configured to removably associate with the proximal opening of the cannula body; and
   wherein the seal structure is configured to retain a positive pressure within the cannula body when engaged with the cannula body, and the seal structure is configured to retain a positive pressure within the cannula body when an object is inserted through the cannula and the seal structure;
   the cannula further including one or more suture attachment structures extending outward laterally from the cannula body; and
   the cannula further including one or more internal recesses in an inner wall of the cannula located directly adjacent to the one or more suture attachment structures, and extending substantially radially outward from the longitudinal axis into the inner wall of the cannula.

2. The surgical cannula of claim 1, wherein:
   the cannula body includes a retaining lip adjacent to the proximal opening that extends outward laterally from the receiving portion; and
   the seal structure is configured to engage with the retaining lip so as to cover the proximal opening.

3. The surgical cannula of claim 1, wherein:
   the cannula body includes
   a first retaining lip located adjacent to the proximal opening and extending outward laterally from the receiving portion,
   a second retaining lip located closer to the distal opening than the first retaining lip and also extending outward laterally from the receiving portion, and
   a retaining groove located between the first retaining lip and the second retaining lip; and
   the seal structure includes a retaining hook structure extending laterally inward from a sidewall of the seal structure, the retaining hook structure being configured to reversibly engage with the retaining groove on the cannula body.

4. The surgical cannula of claim 1, wherein:
   the cannula body is substantially rigid and formed, at least in part, of a material selected from the group consisting of polycarbonate and polypropylene; and
   the insertion portion of the cannula body has a first gauge, the receiving portion of the cannula body has a second gauge, and the second gauge is larger than the first gauge.

5. The surgical cannula of claim 1, wherein
   the first valve and the seal structure are all a continuous unitary piece of an elastomeric material.

6. The surgical cannula of claim 1, wherein:
   the seal structure further includes a tether, and a tab portion;
   the tether including an arm portion connecting the seal structure to a tether ring, the tether ring surrounding the cannula body;
   the tab portion extending laterally outward from the seal structure and being configured to be gripped in order to facilitate removal of the seal structure from the receiving portion of the cannula body; and
   the seal structure, the tether, and the tab portion are all a continuous unitary piece of an elastomeric material.

7. The surgical cannula of claim 1, wherein
   the insertion portion of the cannula body has a first width at the distal opening;
   the insertion portion having a second width at an end of the insertion portion opposite the distal opening;
   wherein the second width is larger than the first width; and
   wherein the insertion portion gradually narrows from the second width to the first width.

8. A method of performing an arthroscopic surgery, comprising:
   inserting the surgical cannula according to claim 1 into an incision in the skin of a patient providing access to a surgical site;
   delivering an implant through the cannula to the surgical site; and
   securing the implant to tissue at the surgical site.

* * * * *